(12) United States Patent
Tanaka et al.

(10) Patent No.: US 7,353,068 B2
(45) Date of Patent: Apr. 1, 2008

(54) CONTROL DEVICE FOR A MEDICAL SYSTEM AND CONTROL METHOD FOR MEDICAL SYSTEM

(75) Inventors: Kazue Tanaka, Sagamihara (JP); Yoshitaka Honda, Hachioji (JP); Hiroo Ono, Koganei (JP)

(73) Assignee: Olympus Corporation, Tokyo (JP)

( * ) Notice: Subject to any disclaimer, the term of this patent is extended or adjusted under 35 U.S.C. 154(b) by 295 days.

(21) Appl. No.: 10/915,222

(22) Filed: Aug. 10, 2004

(65) Prior Publication Data

US 2005/0043828 A1 Feb. 24, 2005

(30) Foreign Application Priority Data

Aug. 19, 2003 (JP) ............................. 2003-295500

(51) Int. Cl.
  G05B 11/01 (2006.01)
  G05B 15/00 (2006.01)
  A61B 18/18 (2006.01)

(52) U.S. Cl. .............................. 700/17; 700/83; 606/42

(58) Field of Classification Search .................. 606/12, 606/38, 169, 34, 1, 126, 42; 715/701, 702; 710/316, 317; 901/5, 6, 9, 23, 30; 700/3, 700/17, 80, 83, 85, 45, 56, 65, 245, 257, 700/260; 600/126
See application file for complete search history.

(56) References Cited

U.S. PATENT DOCUMENTS

| | | | | |
|---|---|---|---|---|
| 5,626,575 A | * | 5/1997 | Crenner | 606/34 |
| 5,788,688 A | * | 8/1998 | Bauer et al. | 606/1 |
| 5,841,631 A | * | 11/1998 | Shin et al. | 361/684 |
| 5,910,139 A | * | 6/1999 | Cochran et al. | 606/1 |
| 6,039,565 A | * | 3/2000 | Chou et al. | 433/29 |
| 6,055,458 A | * | 4/2000 | Cochran et al. | 700/17 |
| 6,285,891 B1 | * | 9/2001 | Hoshino | 455/567 |
| 6,368,269 B1 | * | 4/2002 | Lane | 600/126 |
| 6,666,860 B1 | * | 12/2003 | Takahashi | 606/34 |
| 6,679,875 B2 | * | 1/2004 | Honda et al. | 606/1 |
| 6,830,569 B2 | * | 12/2004 | Thompson et al. | 606/34 |
| 7,217,269 B2 | * | 5/2007 | El-Galley et al. | 606/34 |
| 2001/0029315 A1 | * | 10/2001 | Sakurai et al. | 600/101 |
| 2002/0156466 A1 | | 10/2002 | Sakurai et al. | |
| 2003/0073980 A1 | * | 4/2003 | Finlay et al. | 606/1 |
| 2005/0049458 A1 | * | 3/2005 | Honda et al. | 600/118 |
| 2005/0251228 A1 | * | 11/2005 | Hamel | 607/60 |
| 2006/0217700 A1 | * | 9/2006 | Garito et al. | 606/34 |
| 2007/0016235 A1 | * | 1/2007 | Tanaka et al. | 606/169 |

FOREIGN PATENT DOCUMENTS

| | | | |
|---|---|---|---|
| JP | 07-023978 | | 1/1995 |
| JP | 2799196 | | 7/1998 |
| JP | 11-318916 | | 11/1999 |
| JP | 11-318919 | | 11/1999 |
| JP | 2000-271145 | | 10/2000 |
| JP | 2001178734 A | * | 7/2001 |
| JP | 2001-258089 | | 9/2001 |

* cited by examiner

*Primary Examiner*—David Vincent
*Assistant Examiner*—Jennifer L Norton
(74) *Attorney, Agent, or Firm*—Scully, Scott, Murphy & Presser, PC

(57) ABSTRACT

A control device for a medical system includes: an instructing unit, which can be instructed by an operator, for outputting an instructing signal according to the instruction by the operator; a control signal generating unit for receiving an instructing signal, and generating multiple control signals for controlling multiple medical apparatuses in accordance with the instructing signal; and multiple output units, which can be connected with a medical apparatus, for outputting control signals to the corresponding medical apparatus.

10 Claims, 19 Drawing Sheets

CONTROL DEVICE FOR A MEDICAL SYSTEM AND CONTROL METHOD FOR MEDICAL SYSTEM

CROSS-REFERENCE TO RELATED APPLICATION

This application claims benefit of Japanese Application No. 2003-295500 filed in Japan on Aug. 19, 2003, the contents of which are incorporated by this reference.

BACKGROUND OF THE INVENTION

1. Field of the Invention

The present invention relates to a control device for a medical system, and a control method for controlling a medical system wherein multiple medical apparatuses are controlled by operating switches.

2. Description of the Related Art

Conventionally, there have been electric surgical devices as surgical devices. In recent years, laser surgical devices using a thermal scalpel with a thermal element on the tip of the treatment portion thereof, or a laser beam, have been in practical use as a surgical device. Furthermore, the ultrasonic driving device and the ultrasonic surgical device disclosed in Japanese Unexamined Patent Application Publication No. 2001-258089 have been in practical use.

As various kinds of devices have come to be put to practical use as surgical devices, installing output control switches corresponding all of the surgical devices within an operating room uses up a great deal of space in the operating room, and results in cramped situations.

To end this, a control device for a medical systems which can selectively control multiple surgical devices by operating an output control switch provided on one unit has been proposed in Japanese Unexamined Patent Application Publication No. 11-318916, for example.

Here, multiple surgical devices are selectively operated with a device having an output control switch on one unit thereof.

However, there are cases wherein two surgical devices need to be used simultaneously in order to improve incision capabilities or coagulation capabilities. For example, in a case that high-frequency output of an electric surgical device and ultrasonic output of an ultrasonic surgical device are simultaneously used, the integrated or systemized ultrasonic treatment device disclosed in Japanese Patent No. 2799196 needs to be purchased, for example.

SUMMARY OF THE INVENTION

Accordingly, it is an object of the present invention to provide a control device for a medical system, including a instructing unit for outputting instructing signals corresponding to instructions from an operator, control signal generating means for generating multiple control signals for controlling multiple medical apparatuses according to the instructing signals, and multiple output units, which can be connected with medical apparatuses, for outputting the control signals to corresponding medical apparatuses.

The above and other objects, features and advantages of the invention will become more clearly understood from the following description referring to the accompanying drawings.

BRIEF DESCRIPTION OF THE DRAWINGS

FIGS. 1 through 16G are diagrams for describing a first embodiment of the present invention, wherein:

FIG. 1 is a block diagram for describing the overall configuration of a medical system;

FIG. 2 is a block diagram illustrating the handpiece shown in FIG. 1 in detail;

FIG. 3 is a block diagram illustrating the interior of the output control device shown in FIG. 1;

FIG. 4 is a block diagram illustrating circuits related to data input and output between the respective devices of the medical system;

FIG. 5 is a flowchart illustrating the flow of control of the output control device;

FIG. 6 is an explanatory diagram illustrating setting states of three switch pedals provided on a foot switch in a monopolar singular-selection-output mode;

FIG. 7 is an explanatory diagram illustrating a monitor display example in the monopolar singular-selection-output mode;

FIG. 8 is an explanatory diagram illustrating setting states of the three switch pedals provided on the foot switch in a bipolar singular-selection-output mode;

FIG. 9 is an explanatory diagram illustrating a monitor display example in the bipolar singular-selection-output mode;

FIG. 10 is an explanatory diagram illustrating setting states of the three switch pedals provided on the foot switch in an ultrasonic singular-selection-output mode;

FIG. 11 is an explanatory diagram illustrating a monitor display example in the ultrasonic singular-selection-output mode;

FIG. 12 is an explanatory diagram illustrating setting states of the three switch pedals provided on the foot switch in a monopolar-and-ultrasonic simultaneous-output mode;

FIG. 13 is an explanatory diagram illustrating a monitor display example in the monopolar-and-ultrasonic simultaneous-output mode;

FIG. 14 is an explanatory diagram illustrating setting states of the three switch pedals provided on the foot switch in a bipolar-and-ultrasonic simultaneous-output mode;

FIG. 15 is an explanatory diagram illustrating a monitor display example in the bipolar-and-ultrasonic simultaneous-output mode;

FIGS. 16A through 16G are timing charts illustrating a control signal output from the output control device at simultaneous output of medical apparatuses;

FIG. 16A is a diagram illustrating a foot switch signal caused by operation of the switch pedal of the foot switch;

FIG. 16B is a diagram illustrating monopolar output or bipolar output of the ESU regarding a case wherein an ESU and an ultrasonic surgical device consecutively and simultaneously perform output;

FIG. 16C is, a diagram illustrating ultrasonic output from an ultrasonic surgical device 5 regarding a case wherein an ESU and an ultrasonic surgical device consecutively and simultaneously perform output;

FIG. 16D is a diagram illustrating monopolar output or bipolar output of the ESU regarding a case wherein incision is performed following an affected portion being sufficiently coagulated;

FIG. 16E is a diagram illustrating ultrasonic output from the ultrasonic surgical device regarding a case wherein incision is performed following an affected portion being sufficiently coagulated;

FIG. 16F is a diagram illustrating monopolar output or bipolar output of the ESU in a case of improving incision capabilities as to an affected portion;

FIG. 16G is a diagram illustrating ultrasonic output from the ultrasonic surgical device in a case of improving incision capabilities as to an affected portion;

FIGS. 17 and 18 are diagrams describing a second embodiment of the present invention, wherein:

FIG. 17 is a block diagram illustrating the interior of the output control device;

FIG. 18 is a flowchart illustrating the flow of control of the output control device;

FIGS. 19 through 24 are diagrams describing a third embodiment of the present invention, wherein:

FIG. 19 is a block diagram for describing the overall configuration of the medical system;

FIG. 20 is an explanatory diagram illustrating a setting state of the three switch pedals provided on the foot switch in a two-handpiece selection example with mode selection;

FIG. 21 is an explanatory diagram illustrating a setting state of the three switch pedals provided on the foot switch in a two-handpiece selection example without mode selection;

FIG. 22 is a block diagram illustrating a first holding detection example of the handpiece;

FIG. 23 is a block diagram illustrating a second holding detection example of the handpiece;

FIG. 24 is a flowchart illustrating the flow of control of the output control device;

FIGS. 25 through 27 are diagrams describing a fourth embodiment of the present invention, wherein:

FIG. 25 is an explanatory diagram illustrating initial settings of a front panel of the output control device when turning power on;

FIG. 26 is an explanatory diagram illustrating the setting of the switch pedal of the foot switch at power on and at output operation; and FIG. 27 is a flowchart illustrating the flow of control of the output control device at output setting immediately after turning power on.

DESCRIPTION OF THE PREFERRED EMBODIMENTS

Hereafter, description will be made regarding embodiments of the present invention with reference to drawings.

First Embodiment

A first embodiment of the present invention will be described with reference to FIG. 1 through FIG. 16G.

Figure 1:
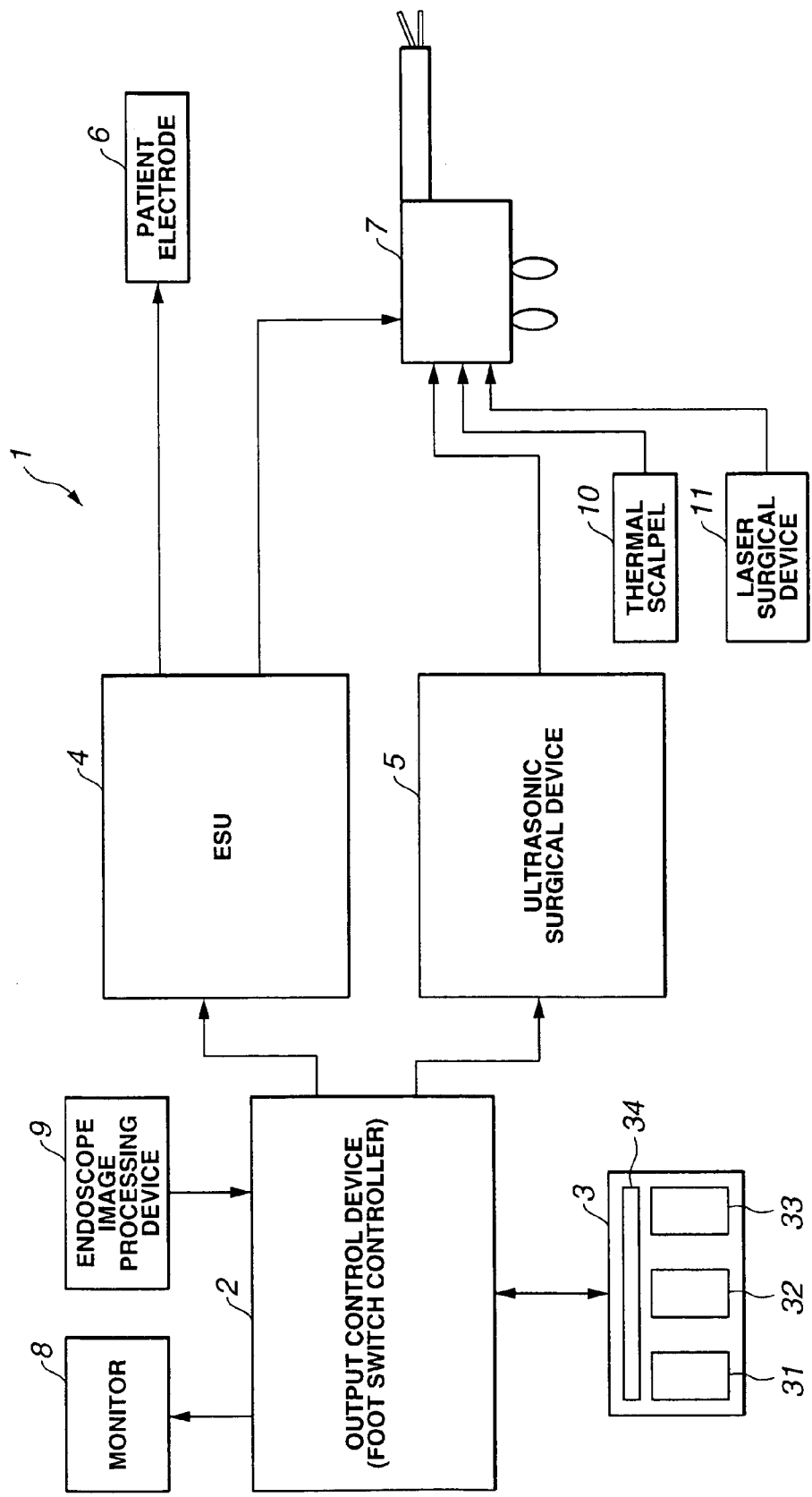

As shown in FIG. 1, a medical system 1 mainly comprises an output control device 2, a foot switch 3, an electric surgical device (otherwise known as an electrosurgical unit, hereafter, referred to as "ESU") 4, an ultrasonic surgical device 5, a patient electrode 6, a handpiece 7, a monitor 8, an endoscope image processing device 9, a thermal scalpel 10, and a laser surgical device 11.

The output control device 2 is a control device for a medical system. The ESU 4, the ultrasonic surgical device 5, the thermal scalpel 10, and the laser surgical device 11 are medical apparatuses employed in the medical system 1.

The ESU 4 incises or coagulates an affected portion using a high-frequency current. An unshown high-frequency power output electrode for monopolar output provided on the ESU is connected to the handpiece 7 and the patient electrode 6. A power output electrode for outputting bipolar output of the ESU 4 is also connected to the handpiece 7. The patient electrode 6 is formed with a wide area, and closely contacted with the skin of a patient to be treated.

The ultrasonic surgical device 5 incises or coagulates the affected portion using frictional heat due to ultrasonic vibrations. The thermal scalpel 10 incises or coagulates the affected portion using heat-emission caused by a heat-emission element. The laser surgical device 11 treats the affected portion using a laser beam.

The endoscope image processing device 9 generates video signals for output of endoscope images taken by an endoscope (not shown) to the monitor 8, and then outputs the signals to the output control device 2.

The output control device 2 controls the foot switch 3, superimposes a symbol for display on the above-described endoscope image so as to display the setting state of switch pedals of the foot switch 3 on the monitor 8, and then generates a signal for displaying the state on the monitor 8. In other words, the output control device 2 works as a foot switch controller.

The monitor 8 displays the endoscope image of a portion to be operated, the settings of the switch pedals of the foot switch 3, and the selected mode based on the signal output from the output control device 2.

The foot switch 3 controls output of the ESU 4, the output of the ultrasonic surgical device 5, the output of the thermal scalpel 10, and the output of the laser surgical device 11 via the output control device 2, and selects an output device. The foot switch 3 includes three switch pedals 31, 32, and 33.

The handpiece 7 receives output from the ESU 4, the ultrasonic surgical device 5, the thermal scalpel 10, and the laser surgical device 11.

Note that the handpiece 7 may receive output from a surgical device which is a medical apparatus capable of connecting to the output control device 2. However, hereinafter, description will be made restricted to a case wherein the handpiece 7 receives output from two medical apparatuses such as the ESU 4 and the ultrasonic surgical device 5 for the sake of facilitating explanation. Accordingly, solid lines representing that the output control device 2 is connected to the thermal scalpel 10, and also connected to the laser surgical device 11 are omitted in FIG. 1.

Description will be made regarding the configuration of the handpiece 7 in detail with reference to FIG. 2.

Figure 2:
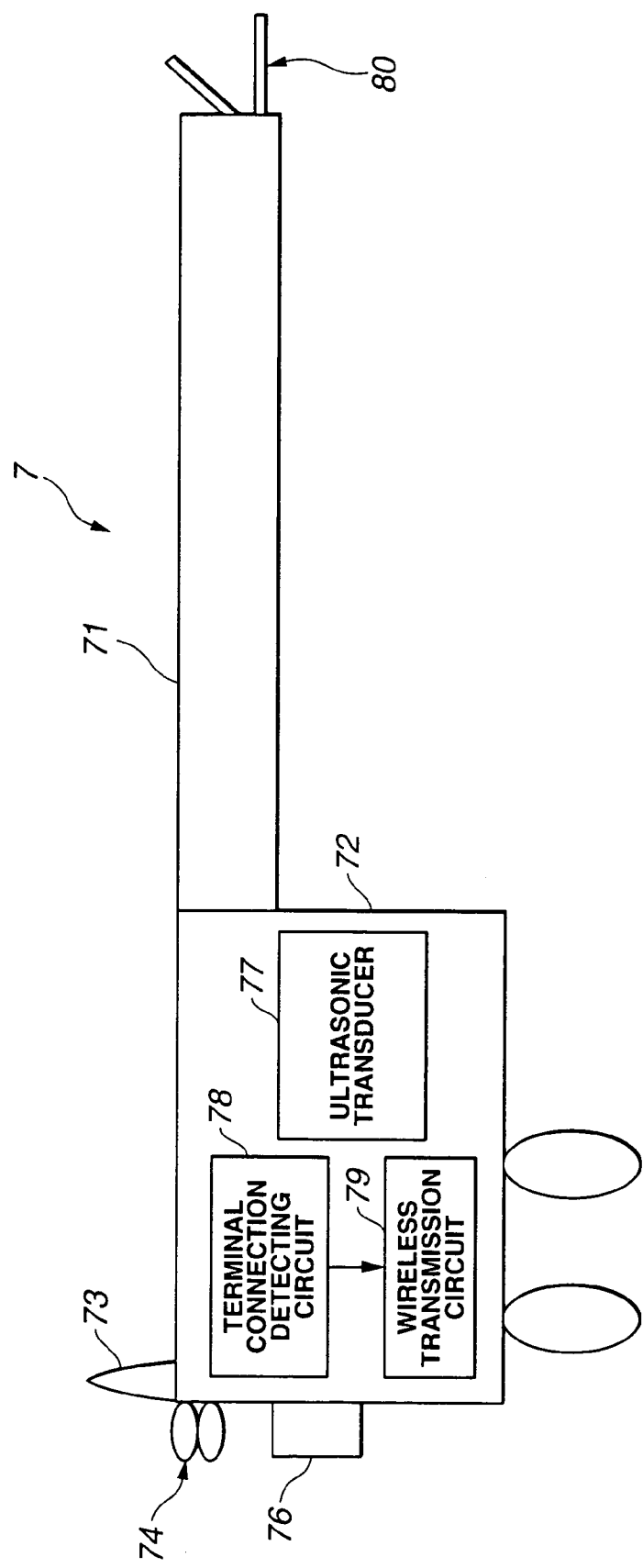

As shown in FIG. 2, the handpiece 7 includes a long and slender sheath 71, and an operating unit 72 doubling as a grip provided on the base edge side of the sheath 71.

The operating unit 72 of the handpiece 7 includes a monopolar-purpose terminal 73, a bipolar-purpose terminal 74, an ultrasonic surgical device-purpose terminal 76, an ultrasonic transducer 77, a terminal connection detecting circuit 78, and a wireless transmission circuit 79. A treatment unit 80 is provided on the tip of the sheath 71 of the handpiece 7.

The monopolar-purpose terminal 73 receives monopolar output from the ESU 4, the bipolar-purpose terminal 74 receives bipolar output from the ESU 4, and the ultrasonic surgical device-purpose terminal 76 receives voltage and current signals output from the ultrasonic surgical device 5, and then supplies the signals to the ultrasonic transducer 77 within the handpiece 7.

The ultrasonic transducer 77 converts the voltage and current signals output from the ultrasonic surgical device 5 into mechanical vibrations, and then vibrates a probe making up the treatment unit 80 fastened thereto.

The monopolar-purpose terminal 73, the bipolar-purpose terminal 74, and the ultrasonic surgical device-purpose terminal 76 each include a switching function, for example. Thus, upon an output line extending from the device being connected to the terminals 73, 74, and 76, a signal indicating that the output line is connected to the terminals 73, 74, and 76 is transmitted from the connected terminal to the terminal connection detecting circuit 78.

The terminal connection detecting circuit 78 takes advantage of this to detect whether or not the monopolar-purpose terminal 73, the bipolar-purpose terminal 74, and the ultrasonic surgical device-purpose terminal 76 are each connected to an output device.

The wireless transmission circuit 79 receives output from the terminal connection detecting circuit 78, and transmits information expressing that output from which of the output devices is connected, to the output control device 2.

The treatment unit 80 subjects a portion to be treated, such as a portion to be operated, to medical treatment using heat-emission due to output supplied from the monopolar-purpose terminal 73 or the bipolar-purpose terminal 74, or ultrasonic vibration due to output supplied from the ultrasonic surgical device-purpose terminal 76.

Figure 3:
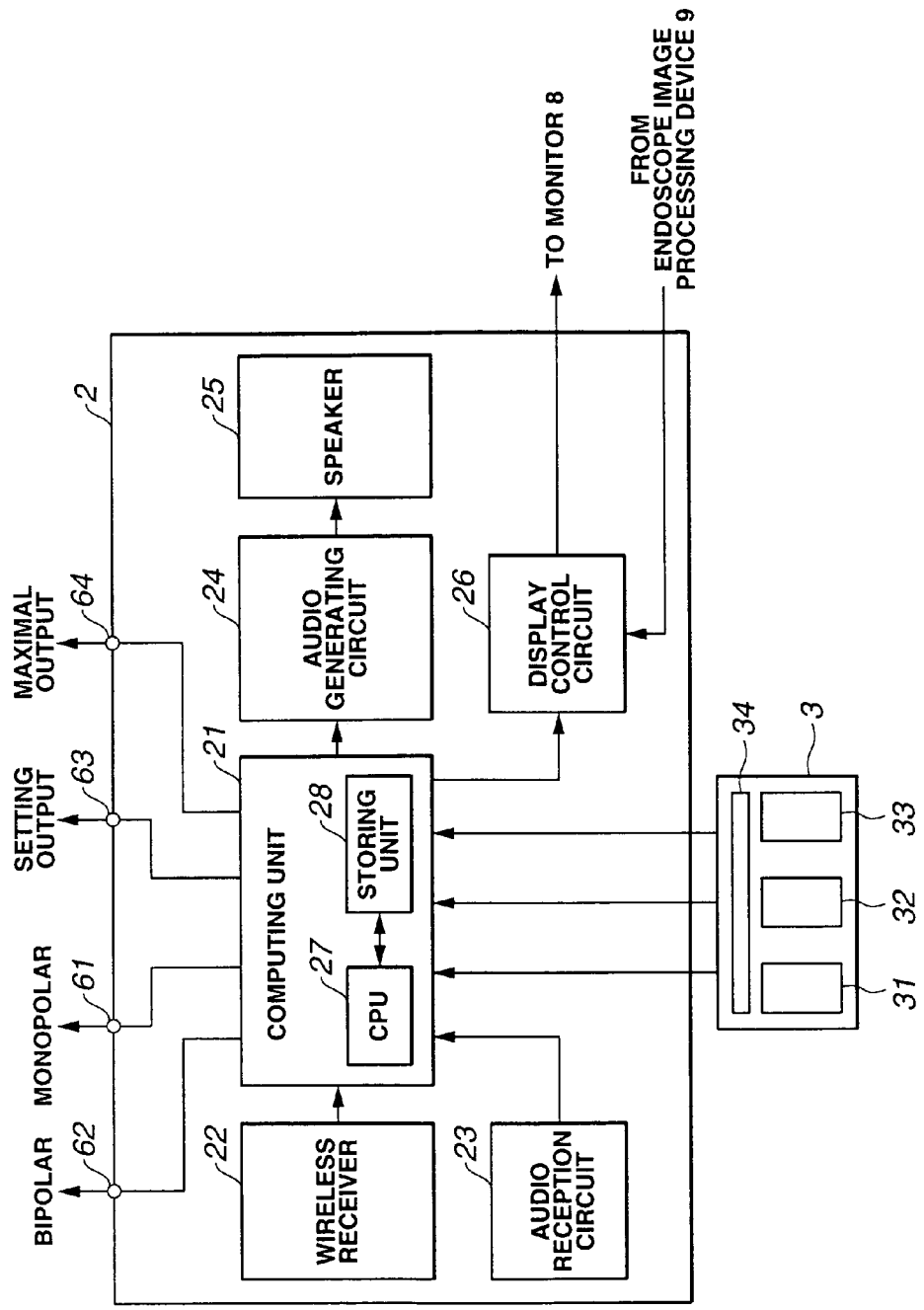

Next, description will be made regarding the inside of the output control device 2 with reference to FIG. 3. As shown in FIG. 3, the output control device 2 includes a computing unit 21, a wireless receiver 22, an audio reception circuit 23, an audio generating circuit 24, a speaker 25, and a display control circuit 26.

The computing unit 21, in response to output from the foot switch 3, generates an on/off control signal for controlling output from the ESU 4 and the ultrasonic surgical device 5. More specifically, the computing unit 21 introduces the on/off control signal of monopolar output from the ESU 4 to an output terminal 61, and also introduces the on/off control signal of bipolar output from the ESU 4 to an output terminal 62. The computing unit 21 further introduces the on/off control signal of setting output from the ultrasonic surgical device 5 to an output terminal 63, and also introduces the on/off control signal of maximal output from the ultrasonic surgical device 5 to an output terminal 64.

The wireless receiver 22 receives a signal from the wireless transmission circuit 79 provided in the handpiece 7 shown in FIG. 2. The audio reception circuit 23 accepts control due to audio from the outside of the device. The audio generating circuit 24, in accordance with a signal from the computing unit 21, generates a signal to the speaker 25.

The display control circuit 26 generates characters corresponding to signals from the endoscope image processing device 9 and the selected output mode (monopolar, bipolar, or ultrasonic surgical device), performs superimposition, and then generates a signal transmitted to the monitor 8.

The computing unit 21 has a configuration including a CPU 27 and a storing unit 28. The storing unit 28 stores pedal setting data (hereafter, referred to as MAP data) corresponding to each output mode. The CPU 27 executes real processing based on the data stored in the storing unit 28.

The switch pedal 31 of the foot switch 3 is assigned to a mode selecting switch for performing mode selection of the output mode (monopolar, bipolar, or ultrasonic surgical device). On the other hand, the switch pedals 32 and 33 of the foot switch 3 are assigned to an output switch for controlling on/off of real output at the time of each mode selection.

More specifically, the switch pedal 32 is used for on/off operations of monopolar output from the ESU 4, setting output from the ultrasonic surgical device 5, and so forth. Here, the ultrasonic surgical device 5 has a configuration wherein an electric signal for vibrating the ultrasonic transducer 77 can be converted to an output value so as to become a predetermined amplitude value of the probe, which is set by keyboard input or the like beforehand. The output in this case is referred to as setting output.

The switch pedal 33 is also used for on/off operations of bipolar output from the ESU 4, maximal output of the ultrasonic surgical device 5, and so forth. Here, the ultrasonic surgical device 5 has a mode for enabling the amplitude of the probe to be set to maximal setting regardless of setting output. The output in this case is referred to as maximal amplitude.

Note that an arrangement may be made wherein a liquid crystal display (hereafter, referred to as LCD) 34 is provided on the foot switch 3, and the pedal setting assigned to the output control device 2 is displayed on the LCD 34.

Next, description will be made regarding a circuit system for confirming the connection between the ESU 4 and the handpiece 7, or the connection between the ultrasonic surgical device 5 and the handpiece 7 with reference to FIG. 4.

Figure 4:
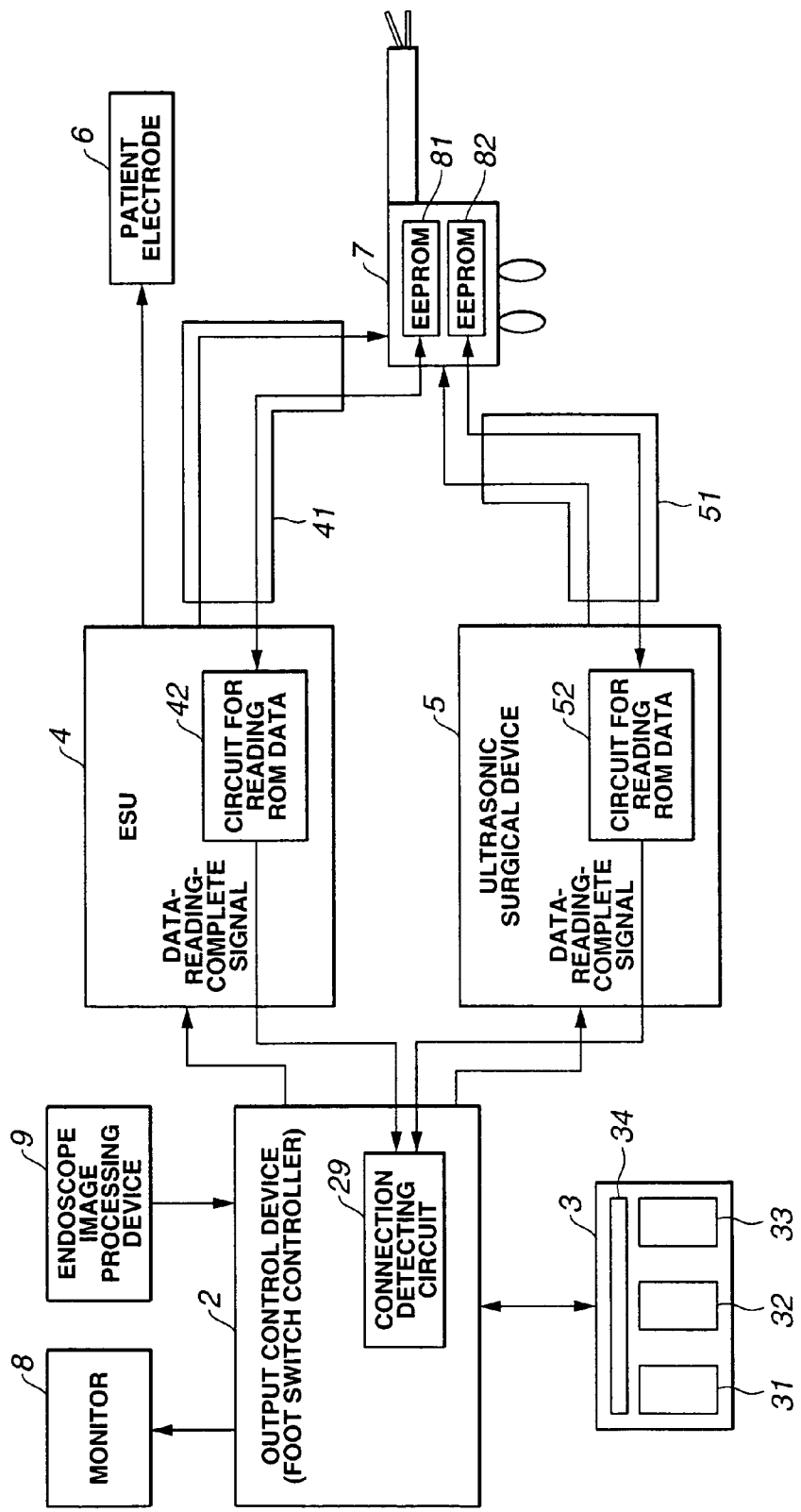

As shown in FIG. 4, the output control device 2 includes a connection detecting circuit 29. The handpiece 7 includes EEPROMs 81 and 82 serving as nonvolatile information recording means, which can be written electrically. The EEPROMs 81 and 82 each store, for example, the serial number, the maximal voltage, the maximal current, the error history, and so forth of the handpiece 7, which are the data to be transmitted to the ESU 4 and the ultrasonic surgical device 5 to be connected to the handpiece 7.

Note that an arrangement may be made wherein flash memory having generally the same function as that of the EEPROMs 81 and 82, or other programmable logic device is employed instead of the EEPROMs 81 and 82. In a case that a power source is mounted on the handpiece 7 side, synchronous dynamic RAM, RAM, and the like may be employed instead of EEPROMs 81 and 82.

A connection cord 41 is a cord for integrating the output lines from the ESU 4 and the signal lines for reading data of the EEPROM 81, and a connection cord 51 is a cord for integrating the output lines from the ultrasonic surgical device 5 and the signal lines for reading data of the EEPROM 82.

The ESU 4 includes a ROM-data-reading circuit 42. The ultrasonic surgical device 5 includes a ROM-data-reading circuit 52. The circuits for reading ROM data 42 and 52 each read out from the EEPROMs 81 and 82.

The ROM-data-reading circuit 42 of the ESU 4, upon the handpiece 7 being connected to the ESU 4 using the connection cord 41, reads out the data from the EEPROM 81. The ROM-data-reading circuit 42, upon readout of the serial data, the maximal voltage, the maximal current, the error history, and so forth from the EEPROM 81 being completed, transmits a data-read-completed signal to the connection detecting circuit 29 of the output control device 2.

The connection detecting circuit 29 detects a state wherein the handpiece 7 is connected to the ESU 4 using the connection cord 41, by detecting the data-read-completed signal output from the ROM-data-reading circuit 42.

Upon the handpiece 7 being connected to the ultrasonic surgical device 5 using the connection cord 51, the ROM-data-reading circuit 52 of the ultrasonic surgical device 5 reads out the data from the EEPROM 82. Upon readout of the serial data, and so forth from the EEPROM 82 being completed, the ROM-data-reading circuit 52 transmits a data-read-completed signal to the connection detecting circuit 29 of the output control device 2.

The connection detecting circuit 29 detects a state wherein the handpiece 7 is connected to the ultrasonic surgical device 5 using the connection cord 51 by detecting the data-read-completed signal output from the ROM-data-reading circuit 52.

When the ESU 4 is not in a state for output, the ROM-data-reading circuit 42 of the ESU 4 periodically reads out the ROM data from the EEPROM 81 for every second, for example. In this state, the connection detecting circuit 29 confirms a connection state between the ESU 4 and the handpiece 7 by detecting the data-read-completed signal from the ROM-data-reading circuit 42.

When the ultrasonic surgical device 5 is not in a state for output, the ROM-data-reading circuit 52 of the ultrasonic surgical device 5 periodically reads out the ROM data from the EEPROM 82 for every second, for example. In this state, the connection detecting circuit 29 confirms a connection state between the ultrasonic surgical device 5 and the handpiece 7 by detecting the data-read-completed signal from the ROM-data-reading circuit 52.

Operation

Figure 5:
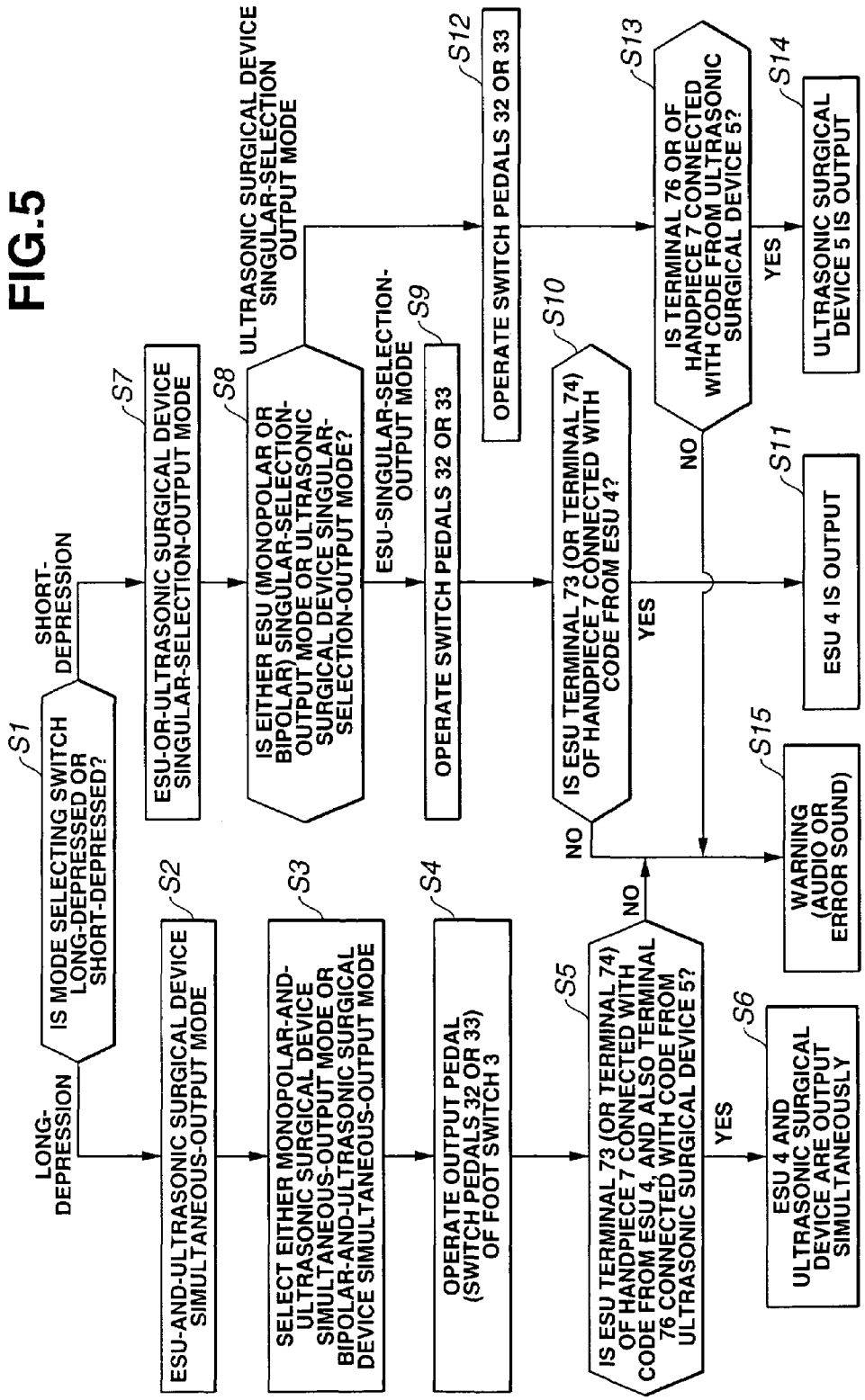

Description will be made regarding control procedures of the output control device 2 in accordance with operations of the foot switch 3 with reference to FIG. 5.

When power source of the output control device 2 is turned on, the computing unit 21 of the output control device 2 is in a state wherein operations thereof are not accepted even if the switch pedal 32 or 33 of the foot switch 3 is operated. In other words, only operations of the switch pedal 31 are accepted, as shown in Step S1.

In Step S1 serving as an instructing signal generating step, in a case that the switch pedal 31 is operated, the computing unit 21 determines whether the switch pedal 31 is depressed for 1 second or longer, i.e., long-depressed, or for less than 1 second, i.e., short-depressed.

If the switch pedal 31 is long-depressed, the computing unit 21 proceeds to processing in Step S2, and then selects an ESU-and-ultrasonic simultaneous-output mode. On the other hand, if the switch pedal 31 is short-depressed in Step S1, the computing unit 21 proceeds to processing in Step S7, and then selects an ESU-and-ultrasonic singular-selection-output mode.

That is to say, the computing unit 21 enables operations of the switch pedals 32 and 33 of the foot switch 3 only after the selection in Step S1.

In Step S2, following the ESU-and-ultrasonic simultaneous-output mode being selected, the computing unit 21 selects either a monopolar-and-ultrasonic simultaneous-output mode or bipolar-and-ultrasonic simultaneous-output mode by the operator short-depressing the switch pedal 31, and so forth, as shown in Step S3.

In Step S4, the computing unit 21 detects operations of the switch pedal 32 or the switch pedal 33 by the operator, temporally stores this operation result, and then proceeds to processing in Step S5.

In Step S5 doubling as both a detecting step and transmitting step, the computing unit 21 detects whether or not the surgical device is connected to a terminal for receiving output of the mode selected in the above-described processing, of a monopolar-purpose terminal 73, a bipolar-purpose terminal 74, and an ultrasonic surgical device-purpose terminal 76, which are the three terminals of the handpiece 7. At this time, detection is made based on the reception signal of the wireless receiver 22 shown in FIG. 3, or the detection result of the connection detecting circuit 29 shown in FIG. 4.

In a case that an output cord is not connected to the corresponding output terminal for the selected mode, the computing unit 21 proceeds to processing in Step S15 serving as an warning step, prohibits output thereof while warning with buzzer sound and so forth is given to the operator using the audio generating circuit 24 and the speaker 25, and also a display indicating that output is prohibited is performed on the monitor 8.

On the other hand, in Step S5, in a case that an output cord is connected to the corresponding output terminal for the selected mode, the computing unit 21 proceeds to processing in Step S6 serving as a simultaneous control signal generating step. Then, the computing unit 21 supplies a control signal for controlling the ESU 4 and the ultrasonic surgical device 5 to perform simultaneous output to the ESU 4 and the ultrasonic surgical device 5. In this case, the output from the ultrasonic surgical device 5 in the above-described setting output in the event that the switch pedal 32 has been selected in Step S4, or is the above-described maximal output in the event that the switch pedal 33 has been selected in Step S4.

Though not shown in the drawing, in the event that the operator wants to change from the ESU-and-ultrasonic simultaneous-output mode to the ESU-and-ultrasonic singular-selection-output-mode, the operator needs to long-depress the switch pedal 31 for 1 second or longer, or a like operation. Thus, the selected ESU-and-ultrasonic simultaneous-output mode is released.

Next, description will be made regarding processing in a case that the flow proceeds to Step S7 as a result of the decision made in Step S1.

In Step S7, following the computing unit 21 going to the ESU-and-ultrasonic singular-selection-output mode, the computing unit 21 selects any one of the monopolar singular-selection-output mode using the ESU 4, the bipolar singular-selection-output mode using the ESU 4, and the ultrasonic singular-selection-output mode using the ultrasonic surgical device 5 by the operator short-depressing the switch pedal 31, as shown in Step S8.

The computing unit 21 further identifies the selected output mode. In a case that the identified result is the ESU singular-selection-output mode, which is monopolar or bipolar, the computing unit 21 proceeds to Step S9. On the other hand, in a case that the identified result is the ultrasonic singular-selection-output mode, the computing unit 21 proceeds to processing in Step S12.

In Step S9, the computing unit 21 detects operations of the switch pedal 32 or the switch pedal 33 by the operator, temporarily stores this detection result, and then proceeds to processing in Step S10.

In Step S10 doubling as a detecting step and transmitting step, in a case that the monopolar singular-selection-output mode is selected, the computing unit 21 detects whether or not the monopolar output cord from the ESU 4 is connected to the monopolar-purpose terminal 73 of the handpiece 7 using the wireless receiver 22 or the connection detecting circuit 29 shown in FIG. 4.

In a case that the monopolar output cord from the ESU 4 is not connected to the monopolar-purpose terminal 73 of the handpiece 7, the computing unit 21 proceeds to processing in Step S15, prohibits monopolar output from the ESU 4, and also gives a warning or the like. In a case that the monopolar output cord from the ESU 4 is connected to the monopolar-purpose terminal 73 of the handpiece 7, the computing unit 21 proceeds to processing in Step S11 serving as an individual control signal generating step, and controls the ESU 4 to perform monopolar output.

In a case that the bipolar singular-selection-output mode is selected in Step S10, the computing unit 21 detects whether or not the bipolar output cord from the ESU 4 is connected to the bipolar-purpose terminal 74 of the handpiece 7 using the wireless receiver 22 shown in FIG. 3 or the connection detecting circuit 29 shown in FIG. 4.

In a case that the bipolar output cord from the ESU 4 is not connected to the bipolar-purpose terminal 74 of the handpiece 7, the computing unit 21 proceeds to processing in Step S15, prohibits bipolar output from the ESU 4, and also gives a warning or the like.

On the other hand, in a case that the bipolar output cord from the ESU 4 is connected to the bipolar-purpose terminal 74 of the handpiece 7, the computing unit 21 proceeds to processing in Step S11, and controls the ESU 4 to perform bipolar output.

Note that in both the monopolar singular-selection-output mode and the bipolar singular-selection-output mode, the output from the ESU 4 in Step S11 is incision output in a case that the switch pedal 32 has been selected in Step S9, and is coagulation output in a case that the switch pedal 33 has been selected in Step S9.

Next, description will be made regarding processing in a case that the flow proceeds to Step S12 based on the determination in Step S8.

In Step S12, the computing unit 21 detects operations of the switch pedal 32 or the switch pedal 33 by the operator, temporarily stores this detection result, and then proceeds to the processing in Step S13.

In Step S13 doubling both as a detecting step and transmitting step, the computing unit 21 detects whether or not the ultrasonic output cord from the ultrasonic surgical device 5 is connected to the ultrasonic surgical device-purpose terminal 76 of the handpiece 7 using the wireless receiver 22 shown in FIG. 3 or the connection detecting circuit 29 shown in FIG. 4. In a case that the ultrasonic output cord from the ultrasonic surgical device 5 is not connected to the ultrasonic surgical device-purpose terminal 76 of the handpiece 7, the computing unit 21 proceeds to processing in Step S15, prohibits ultrasonic output from the ultrasonic surgical device 5, and also gives a warning or the like.

On the other hand, in a case that the ultrasonic output cord from the ultrasonic surgical device 5 is connected to the ultrasonic surgical device-purpose terminal 76 of the handpiece 7, the computing unit 21 proceeds to processing in Step S14 which is an individual control signal generating step, and controls the ultrasonic surgical device 5 to perform ultrasonic output.

The output from the ultrasonic surgical device 5 in Step S14 is the above-described setting output in a case that the switch pedal 32 has been selected in Step S12, and is the above-described maximal output in a case that the switch pedal 33 has been selected in Step S12.

Note that in the present embodiment, the ESU-and-ultrasonic simultaneous-output mode has been selected in Step S2, and the switch pedals 32 and 33 of the foot switch 3 has been operated in Step S3. However, an arrangement may be made as a modification of the present embodiment wherein, in a case that an output cord is not connected to the corresponding terminal of the handpiece 7, warning is made at the time of selecting the corresponding mode so as not to select the mode.

Also, in the event that transition from the simultaneous-output mode to the singular-selection-output mode is made, or in the event that transition from the singular-selection-output mode to the simultaneous-output mode is made in Step S1, mode transition may be made by long-depressing the switch pedal 31 of the foot switch 3.

Now, description will be made regarding the switch pedal settings of the foot switch 3 in each mode according to the first embodiment, and the display state on the monitor 8 with reference to FIGS. 6 through 14.

First, description will be made regarding the switch pedal settings of the foot switch 3 and the display state on the monitor 8 in a case that the computing unit 21 selects the monopolar singular-selection-output mode, with reference to FIGS. 6 and 7.

Figure 6:
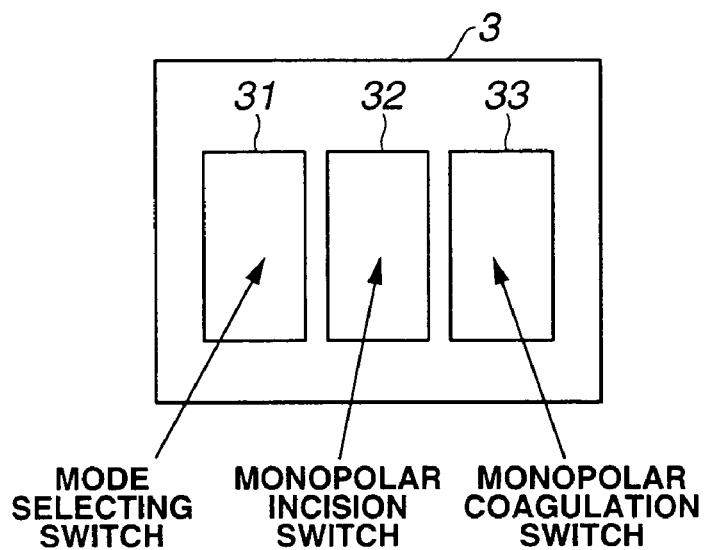

At the monopolar singular selection, i.e., in the monopolar singular-selection-output mode, the switch pedal 31 of the foot switch 3 shown in FIG. 6 has a function as a mode selecting switch.

The switch pedal 32 of the foot switch 3 becomes a monopolar incising switch for controlling the ESU 4 to perform monopolar output for incising an affected portion, and the switch pedal 33 of the foot switch 3 becomes a monopolar coagulating switch for controlling the ESU 4 to perform monopolar output for coagulating an affected portion.

Figure 7:
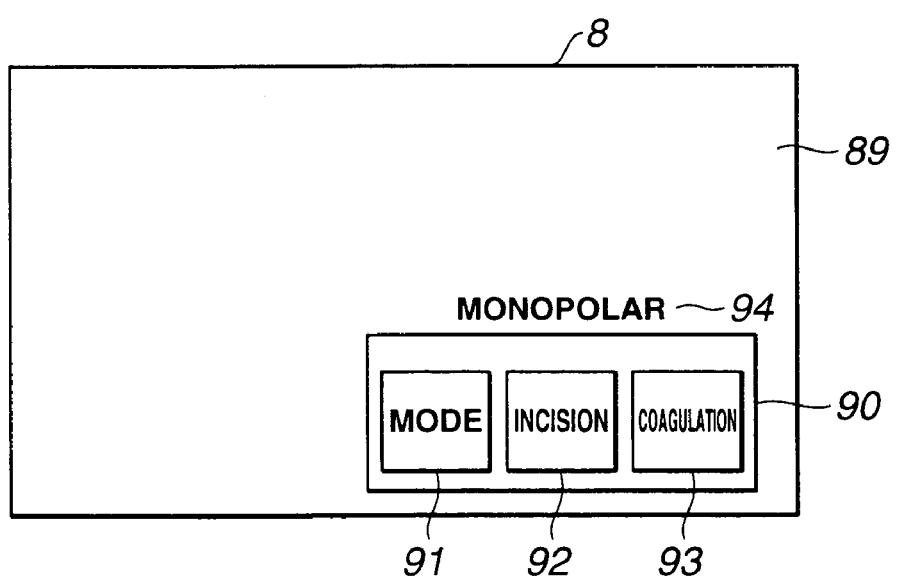

At the lower right of a screen 89 on the monitor 8 for example, as shown in FIG. 7, a character image 90 of the foot switch 3 is displayed. On the character image 90, a character image 91 of the switch pedal 31, a character image 92 of the switch pedal 32, and a character image 93 of the switch pedal 33 are displayed.

The word "MODE" indicating the mode operations is displayed on the character image 91 of the switch pedal 31, the word "CUT" indicating incision is displayed on the character image 92 of the switch pedal 32, and the word "COAG" indicating coagulation is displayed on the character image 93 of the switch pedal 33.

Further, the word 94 "MONOPOLAR" indicating the monopolar singular-selection-output mode is displayed above the character image 90 shown in the screen 89.

Next, description will be made regarding the switch pedal settings of the foot switch 3 and the display state on the monitor 8 in a case that the computing unit 21 selects the bipolar singular-selection-output mode, with reference to FIGS. 8 and 9.

At the bipolar singular selection, i.e., in the bipolar singular-selection-output mode, the switch pedal 31 of the foot switch 3 has a function as a mode selecting switch.

The switch pedal 32 of the foot switch 3 becomes a bipolar incising switch for controlling the ESU 4 to perform bipolar output for incising an affected portion, and the switch pedal 33 of the foot switch 3 becomes a bipolar coagulating switch for controlling the ESU 4 to perform bipolar output for coagulating an affected portion.

Figure 9:
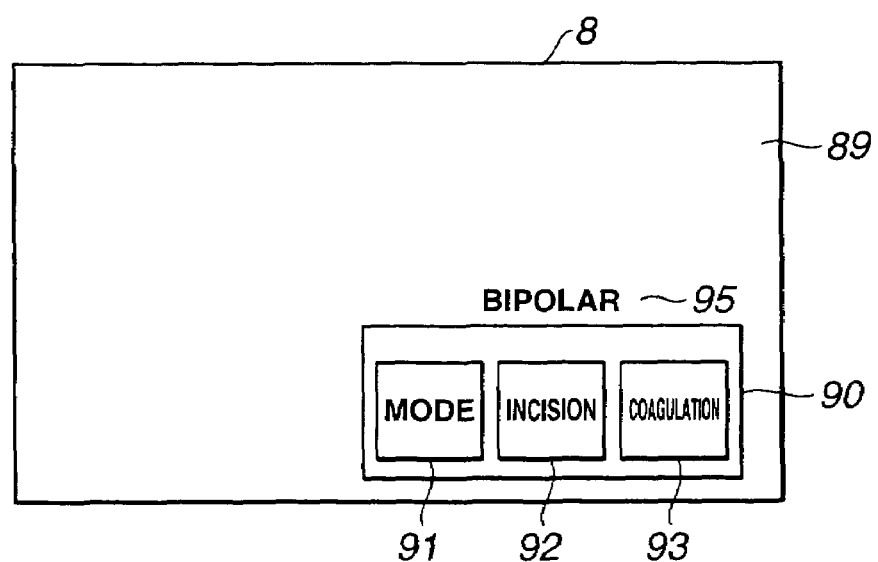

At the lower right of the screen 89 of the monitor 8 for example, as shown in FIG. 9, the character image 90 of the foot switch 3 is displayed, and also the word "MODE" indicating mode operations is displayed on the character image 91 of the switch pedal 31, the word "CUT" indicating incision is displayed on the character image 92 of the switch pedal 32, and the word "COAG" indicating coagulation is displayed on the character image 93 of the switch pedal 33. The word 95 "BIPOLAR" indicating the bipolar singular-selection-output mode is displayed above the character image 90 of the screen 89.

Next, description will be made regarding the pedal settings of the foot switch 3 and the display state on the monitor 8 in a case that the computing unit 21 selects the ultrasonic singular-selection-output mode, with reference to FIGS. 10 and 11.

At the ultrasonic singular selection, i.e., in the ultrasonic singular-selection-output mode, the switch pedal 31 of the foot switch 3 has a function as a mode selecting switch.

The switch pedal 32 of the foot switch 3 becomes an ultrasonic setting output switch for controlling the ultrasonic surgical device 5 to perform ultrasonic setting output, and the switch pedal 33 of the foot switch 3 becomes an ultrasonic maximal output switch for controlling the ultrasonic surgical device 5 to perform ultrasonic maximal output.

Figure 11:
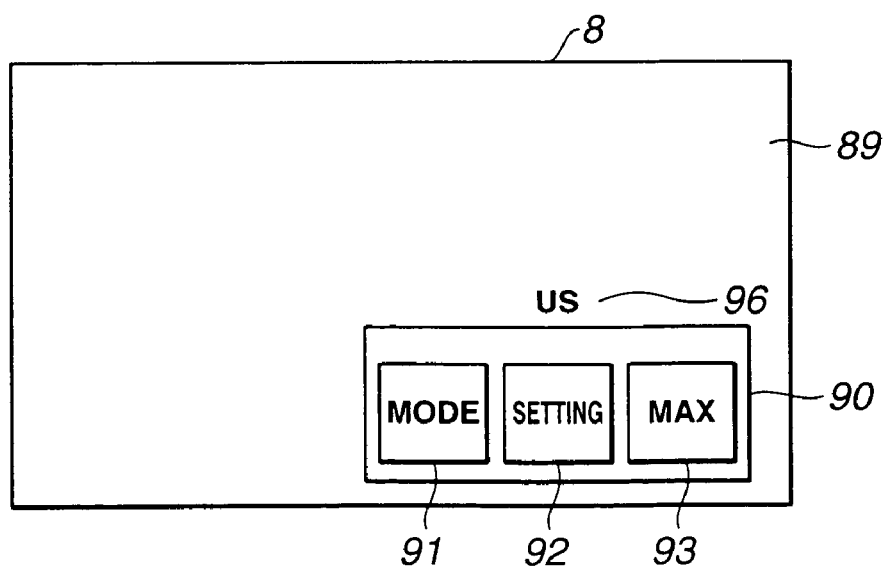

At the lower right of the screen 89 of the monitor 8 for example, as shown in FIG. 11, the character image 90 of the foot switch 3 is displayed, and also the word "MODE" indicating mode operations is displayed on the character image 91 of the switch pedal 31, the word "SETTING" indicating setting output is displayed on the character image 92 of the switch pedal 32, and the word "MAX" indicating maximal output is displayed on the character image 93 of the switch pedal 33. Further, the word 96 "US" indicating the ultrasonic singular-selection-output mode are displayed above the character image 90 of the screen 89.

Next, description will be made regarding the switch pedal settings of the foot switch 3 and the display state on the monitor 8 in a case that the computing unit 21 selects the monopolar-and-ultrasonic simultaneous-output mode, with reference to FIGS. 12 and 13.

Figure 12:
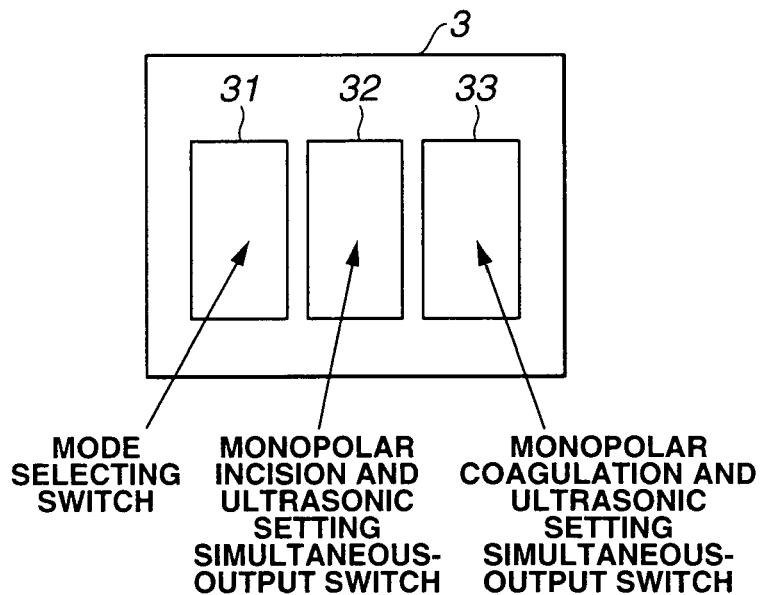

In the monopolar-and-ultrasonic simultaneous-output mode, the switch pedal 31 of the foot switch 3 has a function as a mode selecting switch, as shown in FIG. 12.

The switch pedal 32 of the foot switch 3 becomes a monopolar incision and ultrasonic setting simultaneous output switch for controlling the ESU 4 to perform monopolar output for incising an affected portion, and also controlling the ultrasonic surgical device 5 to perform ultrasonic setting output.

The switch pedal 33 of the foot switch 3 becomes a monopolar coagulation and ultrasonic setting simultaneous output switch for controlling the ESU 4 to perform monopolar output for coagulating an affected portion, and also controlling the ultrasonic surgical device 5 to perform ultrasonic setting output.

Figure 13:
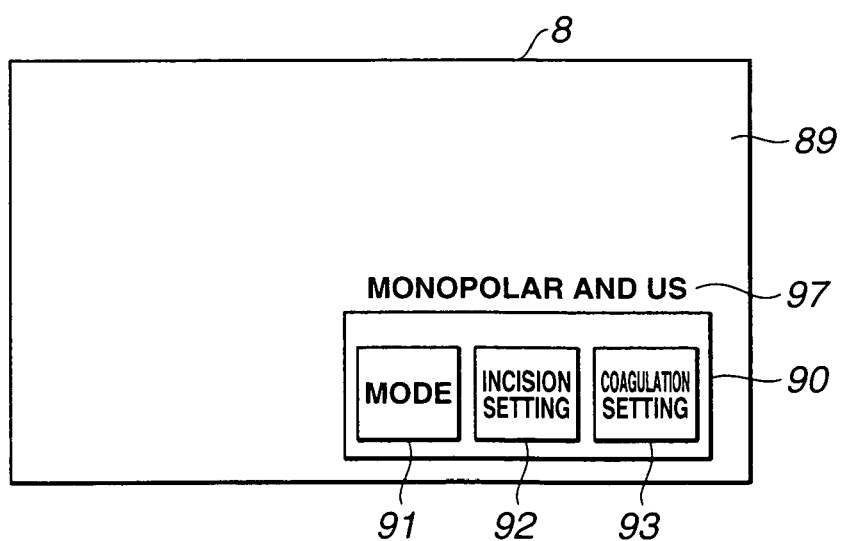

At the lower right of the screen 89 of the monitor 8 for example, as shown in FIG. 13, the character image 90 of the foot switch 3 is displayed, and also the word "MODE" indicating mode operations is displayed on the character image 91 of the switch pedal 31. The word "CUT" indicating incision by the ESU 4 and the word "SETTING" indicating setting output of the ultrasonic surgical device 5 are displayed on the character image 92 of the switch pedal 32. The word "COAG" indicating coagulation by the ESU 4 and the word "SETTING" indicating setting output of the ultrasonic surgical device 5 are displayed on the character image 93 of the switch pedal 33. The words 97 "MONOPOLAR and US" indicating the monopolar-ultrasonic simultaneous-output mode are displayed above the character image 90 of the screen 89.

Finally, description will be made regarding the switch pedal settings of the foot switch 3 and a display state on the monitor 8 in a case that the computing unit 21 selects the bipolar-and-ultrasonic simultaneous-output mode, with reference to FIGS. 14 and 15.

Figure 14:
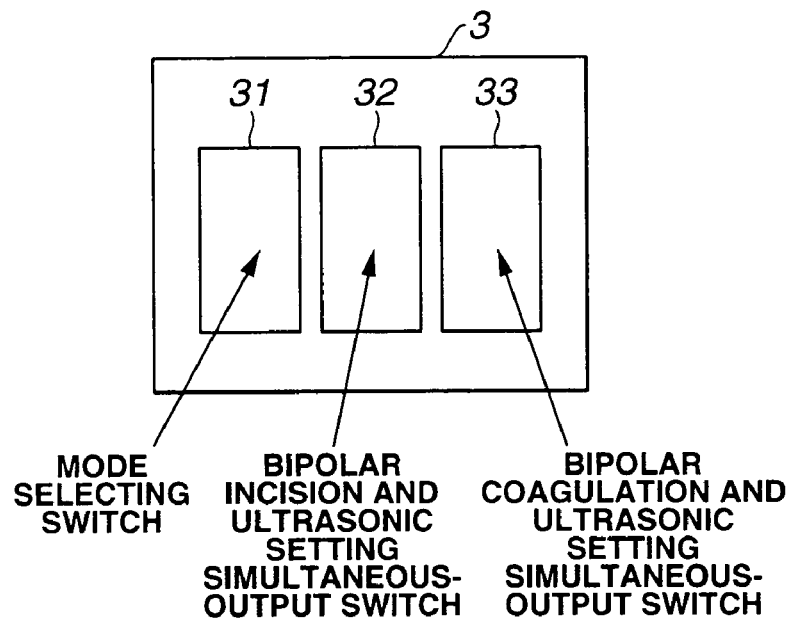

In the bipolar-and-ultrasonic simultaneous-output mode, the switch pedal 31 of the foot switch 3 has a function as a mode selecting switch, as shown in FIG. 14.

The switch pedal 32 of the foot switch 3 becomes a bipolar incision and ultrasonic setting simultaneous output switch for controlling the ESU 4 to perform bipolar output for incising an affected portion, and also controlling the ultrasonic surgical device 5 to perform ultrasonic setting output.

The switch pedal 33 of the foot switch 3 becomes a bipolar coagulation and ultrasonic setting simultaneous output switch for controlling the ESU 4 to perform bipolar output for coagulating an affected portion, and also controlling the ultrasonic surgical device 5 to perform ultrasonic setting output.

Figure 15:
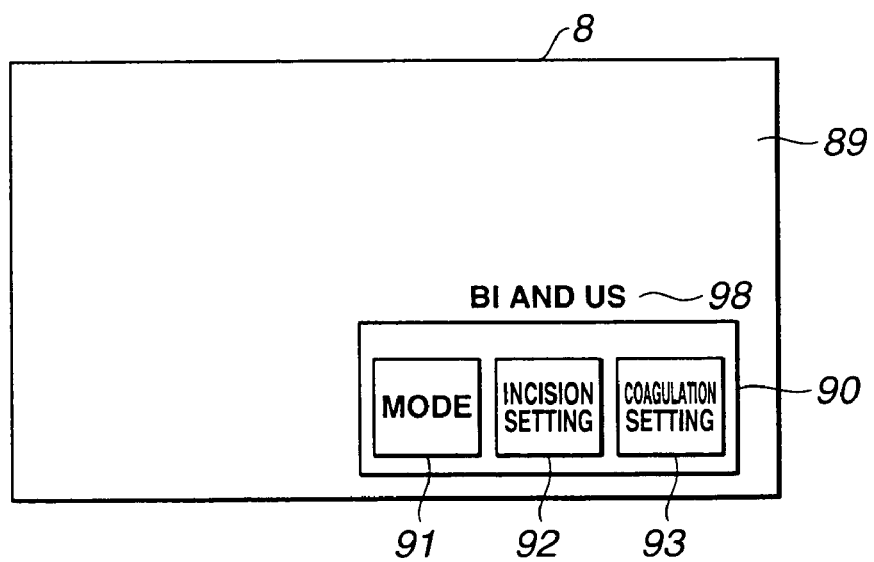
Figure 16:
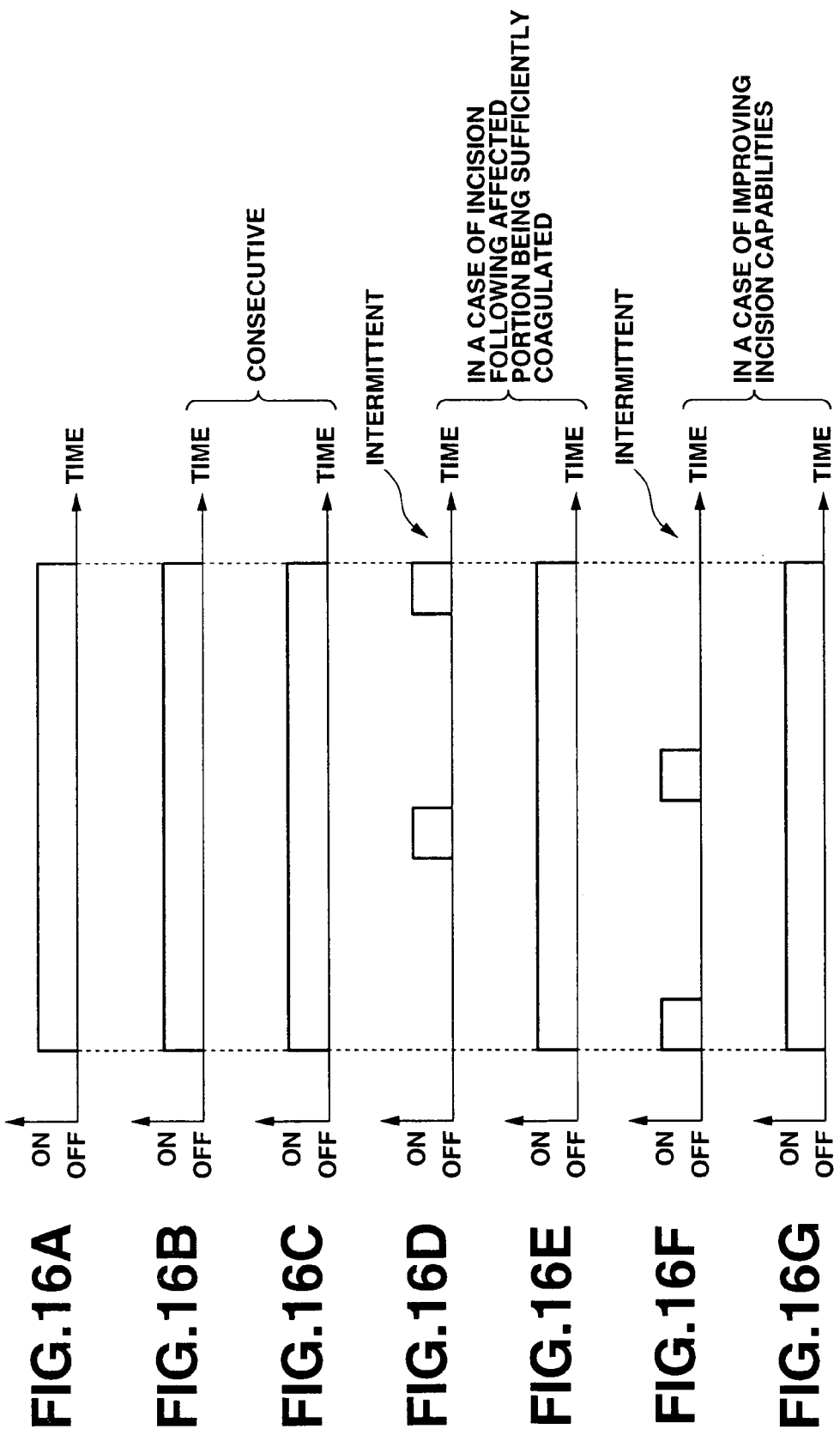

At the lower right of the screen 89 of the monitor 8 for example, as shown in FIG. 15, the character image 90 of the foot switch 3 is displayed, and also the word "MODE" indicating mode operations is displayed on the character image 91 of the switch pedal 31. The word "CUT" indicating incision by the ESU 4 and the word "SETTING" indicating setting output of the ultrasonic surgical device 5 are displayed on the character image 92 of the switch pedal 32. The word "C OAG" indicating coagulation by the ESU 4 and the word "SETTING" indicating setting output of the ultrasonic surgical device 5 are displayed on the character image 93 of the switch pedal 33. The words 98 "BI and US" indicating the bipolar-ultrasonic simultaneous-output mode are displayed above the character image 90 of the screen 89.

As shown in FIGS. 6 through 15, the operator can easily know which mode is selected by performing settings and display, or what kind of output is made by which switch pedal provided on the foot switch 3 is operated.

Next, description will be made regarding control waveforms of the ESU 4 and the ultrasonic surgical device 5 in the ESU-and-ultrasonic simultaneous-output mode with reference to FIGS. 16A through 16G.

In the ordinary affected portion treatment using the ESU-and-ultrasonic simultaneous-output mode, as shown in FIGS. 16B and 16C, the ESU 4 and the ultrasonic surgical device 5 consecutively and simultaneously perform output synchronously with the on-state of the foot switch signal shown in FIG. 16A.

In a case that incision is performed following sufficient coagulation, as shown in FIGS. 16D and 16E, the ultrasonic surgical device 5 starts to output a consecutive ultrasonic waveform synchronously with the on-state of the foot switch signal shown in FIG. 16A, and then the output control device 2 controls the ESU 4 to perform intermittent waveform output.

When improving incising capabilities, as shown in FIGS. 16F and 16G, the output control device 2 controls the ESU 4 to perform intermittent waveform output and the ultrasonic surgical device 5 to perform consecutive ultrasonic waveform output simultaneously. Though not shown in the drawing, in the present embodiment, alternating output may be performed using the ultrasonic surgical device 5 and the ESU 4.

Control of consecutive/intermittent output of output waveforms may be performed by using an output signal from the output control device 2 to the ESU4, and an output signal from the output control device 2 to the ultrasonic surgical device 5 respectively.

In the present embodiment, while mode setting has been performed by operating the switch pedals of the foot switch 3, an arrangement may be made wherein control of mode setting is performed by the operator's voice using the audio reception circuit 23 provided in the output control device 2.

Moreover, in the present embodiment, it is more preferable that consecutive/intermittent operation may be selected based on ease-of-use of the operator, purpose, a portion to be removed, and the like, or may be performed automatically by detecting the impedance of an affected portion.

According to such a configuration and operation, the foot switch 3 shown in FIG. 3 is an instructing unit, which can be instructed by the operator, for outputting an instructing signal corresponding to instructions by the operator.

The computing unit 21, which inputs the above-described instructing signal, is a control signal generating unit serving as control signal generating means for generating a first control signal for controlling the ESU 4 serving as a first medical apparatus, i.e., a monopolar output on/off control signal and a bipolar output-on/off control signal, and a second control signal for controlling the ultrasonic surgical device 5 serving as a second medical apparatus, i.e., a setting output on/off control signal and a maximal output on/off control signal in accordance with the instructing signal.

The output terminals 61 and 62, which can be connected with the first medical apparatus, make up a first output unit for outputting the first control signal to the first medical apparatus.

The output terminals 63 and 64, which can be connected with the second medical apparatus, make up a second output unit for outputting the second control signal to the second medical apparatus.

The computing unit 21 includes simultaneous output control means for controlling multiple medical apparatuses to perform output simultaneously, selection output control means for controlling multiple medical apparatuses to perform output in individual timing, and selecting means capable of selecting control of the two output control means, in accordance with a program stored in the storing unit 28.

The wireless transmission circuit 79 is transmitting means for transmitting the detection result from the terminal connection detecting circuit 78 to the output control device 2. The audio generating circuit 24 and the speaker 25, which are provided on the output control device 2, are warning means for performing warning operations in a case that output control of the corresponding medical apparatus is attempted in a state that the detection result from the transmitting means shows no connection with output from the corresponding medical apparatus.

Advantages

According to the first embodiment, the output control device 2 can readily control the ESU 4 and the ultrasonic surgical device 5 to perform output selectively or simultaneously. Detection is made whether or not the output cord from the ESU 4 or the ultrasonic surgical device 5 is precisely connected to the corresponding connector provided on the handpiece 7, and in a case that the output cord is not properly connected to the connector, warning thereof is made, thereby improving reliability.

Even in a case that there has already been the ESU 4 in a facility such as an operating room, and the ultrasonic surgical device 5 is installed afterwards, simultaneous output can improve coagulating capabilities and incising capabilities by using the low-priced output control device 2 such as shown in the present embodiment.

Thus, the environment wherein simultaneous output of multiple medical apparatuses can be performed can be realized at a low price, and also operation of multiple medical apparatuses can be controlled by switching operations without complicating switching operations, thereby making medical work more efficient.

The control method according to the present embodiment has advantages such that simultaneous output of multiple medical apparatuses can be controlled, and also output of the individual medical apparatus can be selectively controlled, the environment wherein simultaneous output of multiple medical apparatuses can be performed can be realized at a low price, and so forth.

Second Embodiment

Description will be made regarding a second embodiment of the present invention with reference to FIGS. 17 and 18. Note that in the description of the second embodiment using FIGS. 17 and 18, the same components as those in the first embodiment shown in FIGS. 1 thorough 16G will be denoted with the same reference numerals and the description thereof is omitted. With regard to the components of an endoscope system not shown in FIGS. 17 and 18, description will be made with reference to those of FIGS. 1 and 2.

Configuration

The output control device 2 according to the first embodiment shown in FIGS. 1 through 16G performs simultaneous output of the ESU 4 and the ultrasonic surgical device 5, and generates a control signal for each singular selection output, using integrated control of the computing unit 21.

Figure 17:
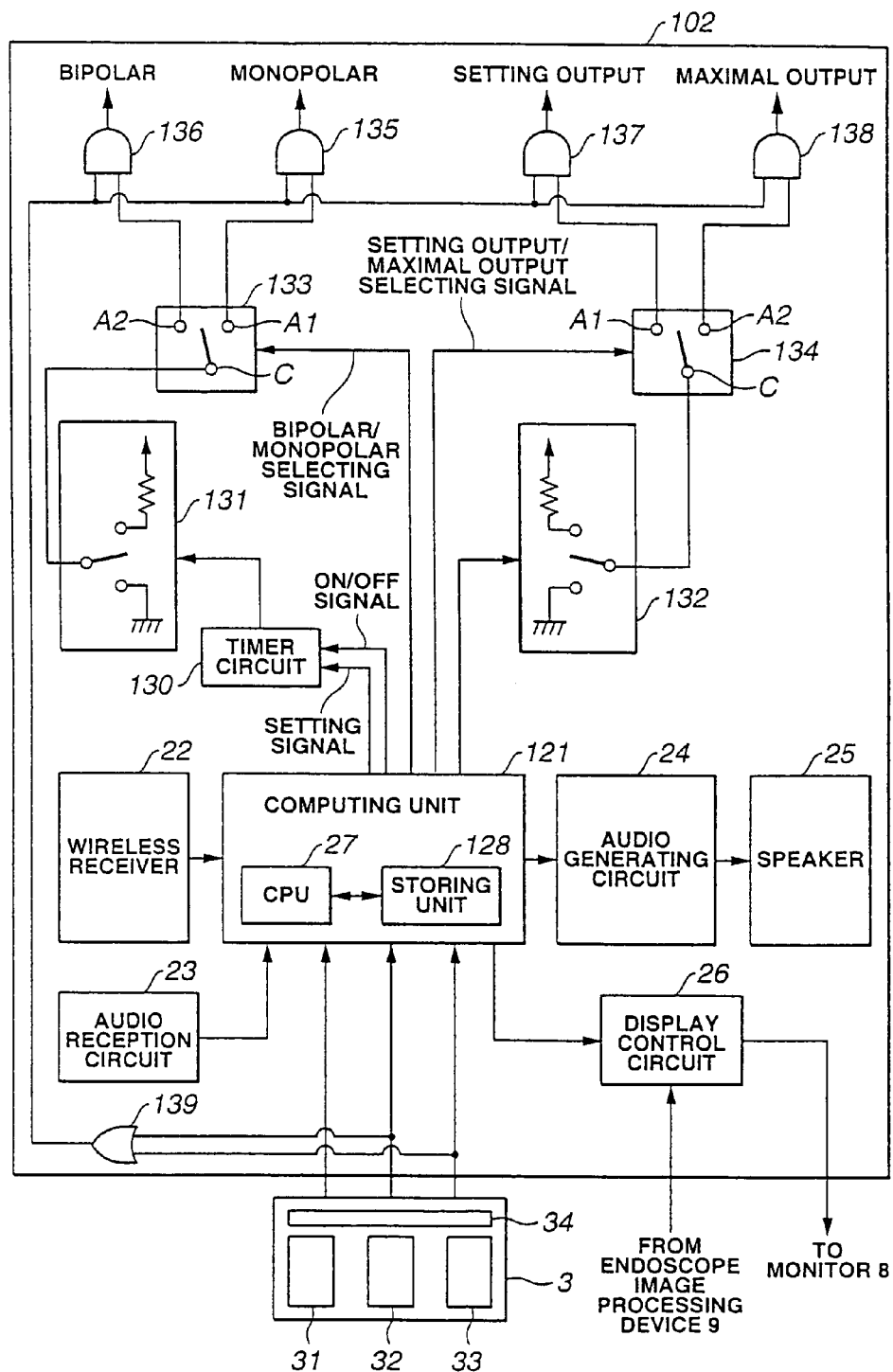
Figure 18:
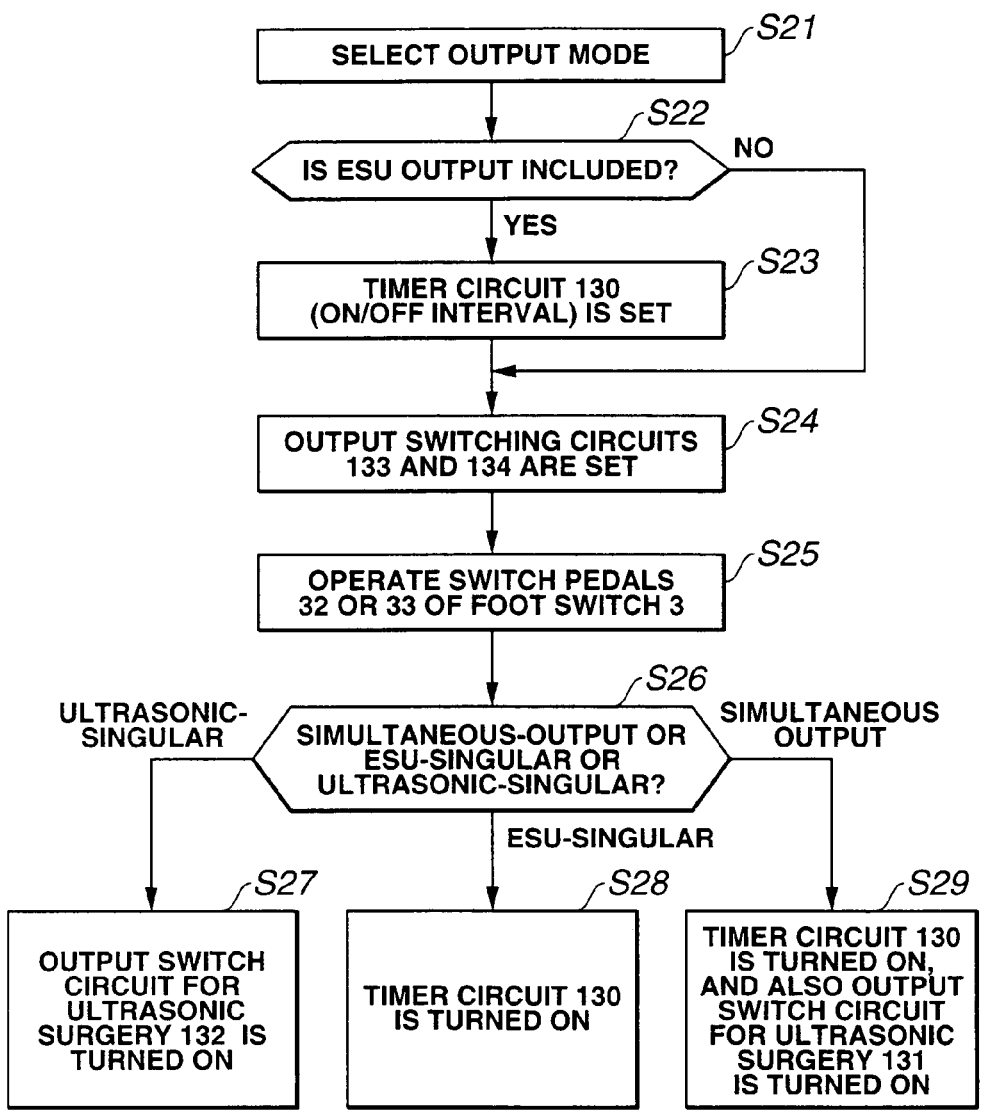

An output control device 102 according to the second embodiment shown in FIG. 17 includes a timer circuit 130, an ESU output switch circuit 131, an ultrasonic surgery output switch circuit 132, output switching circuits 133 and 134, AND circuits 135 through 138 and an OR circuit 139 serving as a protection circuit besides a computing unit 121 which generates the above-described control signal.

The computing unit 121 executes operations different from those in the first embodiment using a control program stored in a storing unit 128.

The timer circuit 130 performs the on/off control of the ESU 4 in the ESU output mode in accordance with instructions from the computing unit 121. In particular, in a case that simultaneous output is performed at the ultrasonic surgical device 5 and the ESU 4, the output from the ESU 4 repeats on/off such as shown in FIGS. 16D and 16F. Start of operation and end of operation regarding the timer circuit 130 are controlled by the on/off signal from the computing unit 121.

The ESU output switch circuit 131 generates an output enable signal serving as an on/off control signal as to the ESU 4, and then outputs the signal from the output terminal thereof, in accordance with the on/off signal from the timer circuit 130.

The ultrasonic surgery output switch circuit 132 generates an output enable signal serving as an on/off control signal as to the ultrasonic surgical device 5, and then outputs the signal from the output terminal thereof, in accordance with the control signal from the computing unit 121.

The output terminal of the ESU output switch circuit 131 is connected to the common terminal C of the output switching circuit 133. The output terminal of the ultrasonic surgery output switch circuit 132 is connected to the common terminal C of the output switching circuit 134. A first output terminal A1 of the output switching circuit 133 is connected to a first input terminal of the AND circuit 135, and a second output terminal A2 of the output switching circuit 133 is connected to a first input terminal of the AND circuit 136. Also, a first output terminal A1 of the output switching circuit 134 is connected to a first input terminal of the AND circuit 137, and a second output terminal A2 of the output switching circuit 134 is connected to a first input terminal of the AND circuit 138.

First through third output terminals of the foot switch 3 output operational output of the corresponding switch pedals 31 through 33 to the computing unit 121. The second and third terminals of the foot switch 3 are further connected to the corresponding first and second input terminals of the OR circuit 139. The output terminal of the OR circuit 139 is connected to second input terminals of the AND circuits 135 through 138.

The output terminals of the AND circuits 135 and 136 are connected to a monopolar output enable signal input terminal and a bipolar output enable signal input terminal of the ESU 4 respectively via the output terminal of the output control device-102.

The output terminals of the AND circuits 137 and 138 are connected to a setting output enable signal input terminal and a maximal output enable signal input terminal of the ultrasonic surgical device 5 respectively, via the output terminal of the output control device 102.

The output switching circuit 133 selects either bipolar output or monopolar output in accordance with the bipolar/monopolar output selecting signal from the computing unit 121.

In a case that the output switching circuit 133 selects monopolar output, the common terminal C is connected to the output terminal A1, the output enable signal from the ESU output switch circuit 131 is led to the first input terminal of the AND circuit 135.

In a case that the output switching circuit 133 selects bipolar output, the common terminal C is connected to the output terminal A2, the output enable signal from the ESU output switch circuit 131 is led to the first input terminal of the AND circuit 136.

In the second embodiment, simultaneous output of bipolar output and monopolar output from the ESU 4 due to malfunction of a circuit such as a runaway malfunction of the computing unit 121 for example, is prevented from occurring by using the above-described output switching circuit 133.

The output switching circuit 134 selects either setting output or maximal output of the ultrasonic surgical device 5 in accordance with the ultrasonic setting/maximal output selecting signal from the computing unit 121.

In a case that the output switching circuit 134 selects setting output of the ultrasonic surgical device 5, the common terminal C is connected to the output terminal A1, and the output enable signal from the ultrasonic surgery output switch circuit 132 is introduced to the first input terminal of the AND circuit 137.

In a case that the output switching circuit 134 selects maximal output of the ultrasonic surgical device 5, the common terminal C is connected to the output terminal A2, the output enable signal from the ultrasonic surgery output switch circuit 132 is introduced to the first input terminal of the AND circuit 138.

In the second embodiment, simultaneous output of setting output and maximal output from the ultrasonic surgical device 5, due to malfunction of a circuit, for example, is prevented from occurring by using the above-described output switching circuit 134.

In the AND circuits 135 through 138, performing the logic operation AND between output from the output switching circuit 133 and the on/off signal output from the foot switch 3, or between output from the output switching circuit 134 and the on/off signal output from the foot switch 3 prevents the output enable signal from turning on due to malfunction of the previous-stage circuit. In other words, only when the switch pedal 32 or the switch pedal 33 of the foot switch 3 is on, the output enable signal is set so as to be on.

Operation

Description will be made regarding processing from mode selection to generation of the output enable signal in the second embodiment with reference to the flowchart in FIG. 18.

The output mode is selected by operating the switch pedal 31 in Step S21, the computing unit 121 proceeds to processing in Step S22.

In Step S22, the computing unit 121 determines whether or not the selected mode includes output from the ESU 4. Here, in a case of the mode including output from the ESU 4, the computing unit 121 proceeds to processing in Step S23.

In Step S23, the computing unit 121 sets on/off of the timer circuit 130 using a setting signal, and then proceeds to processing in Step S24. Here, in a case of consecutive output, the computing unit 121 sets the off interval of the ESU output switch circuit 131 to zero.

On the other hand, in a case of the mode excluding output from the ESU 4 in Step S22, i.e., in a case of the mode only including output from the ultrasonic surgical device 5, the computing unit 121 skips on/off setting of the timer circuit 130, and then proceeds to processing in Step S24. In Step S24, the computing unit 121 performs setting of the output switching circuits 133 and 134 based on the selected output mode.

Next, upon the switch pedals 32 and 33 of the foot switch 3 being operated in Step S25, the computing unit 121 identifies the selected output mode such as shown in Step S26. Then, the computing unit 121 proceeds to processing of any one of Steps S27 through S29 depending on the identified output mode.

When the identified result of the selected output mode in Step S26 is the ultrasonic singular-selection-output mode, the computing unit 121 sets the ultrasonic surgery output switch circuit 132 to an on-state in Step S27. In a case that the switch pedal 32 is operated, the computing unit 121 controls the AND circuit 137 to output a setting output enable signal. On the other hand, in a case that the switch pedal 33 is operated, the computing unit 121 controls the AND circuit 138 to output a maximal output enable signal.

When the identified result of the selected output mode in Step S26 is the ESU singular-selection-output mode, the computing unit 121 sets the timer circuit 130 to an on-state in Step S28. In a case that the switch pedal 32 is operated, the computing unit 121 controls the AND circuit 135 to output a monopolar output enable signal. On the other hand, in a case that the switch pedal 33 is operated, the computing unit 121 controls the AND circuit 136 to output a bipolar output enable signal.

Further, when the identified result of the selected output mode in Step S26 is the ESU-and-ultrasonic simultaneous-output mode, the computing unit 121 sets the timer circuit 130 and the ultrasonic surgery output switch circuit 132 to an on-state in Step S29. In a case that the switch pedal 32 is operated, the computing unit 121 controls the AND circuit 135 to output a monopolar output enable signal, and also controls the AND circuit 137 to output a setting output enable signal.

On the other hand, in a case that the switch pedal 33 is operated, the computing unit 121 controls the AND circuit 136 to output a bipolar output enable signal, and also controls the AND circuit 138 to output a maximal output enable signal.

Thus, only when the switch pedals 32 and 33 of the foot switch 3 are on, the ESU 4 and the ultrasonic surgical device 5 are set so as to perform output.

Advantages

The second embodiment obtains the same advantages as that in the first embodiment, prevents the ESU 4 from simultaneous output of bipolar output and monopolar output due to malfunction of a circuit, prevents the ultrasonic surgical device 5 from simultaneous output of setting output and maximal output, and controls the ESU 4 or the ultrasonic surgical device 5 to perform output only when the foot switch 3 is on, thereby further improving the reliability of the medical system.

Third Embodiment

Description will be made regarding a third embodiment of the present invention with reference to FIGS. 19 through 24. Note that in the description of the third embodiment using FIGS. 19 through 24, the same components as those in the first embodiment shown in FIGS. 1 thorough 16G will be denoted with the same reference numerals and the description thereof is omitted.

Configuration

Figure 19:
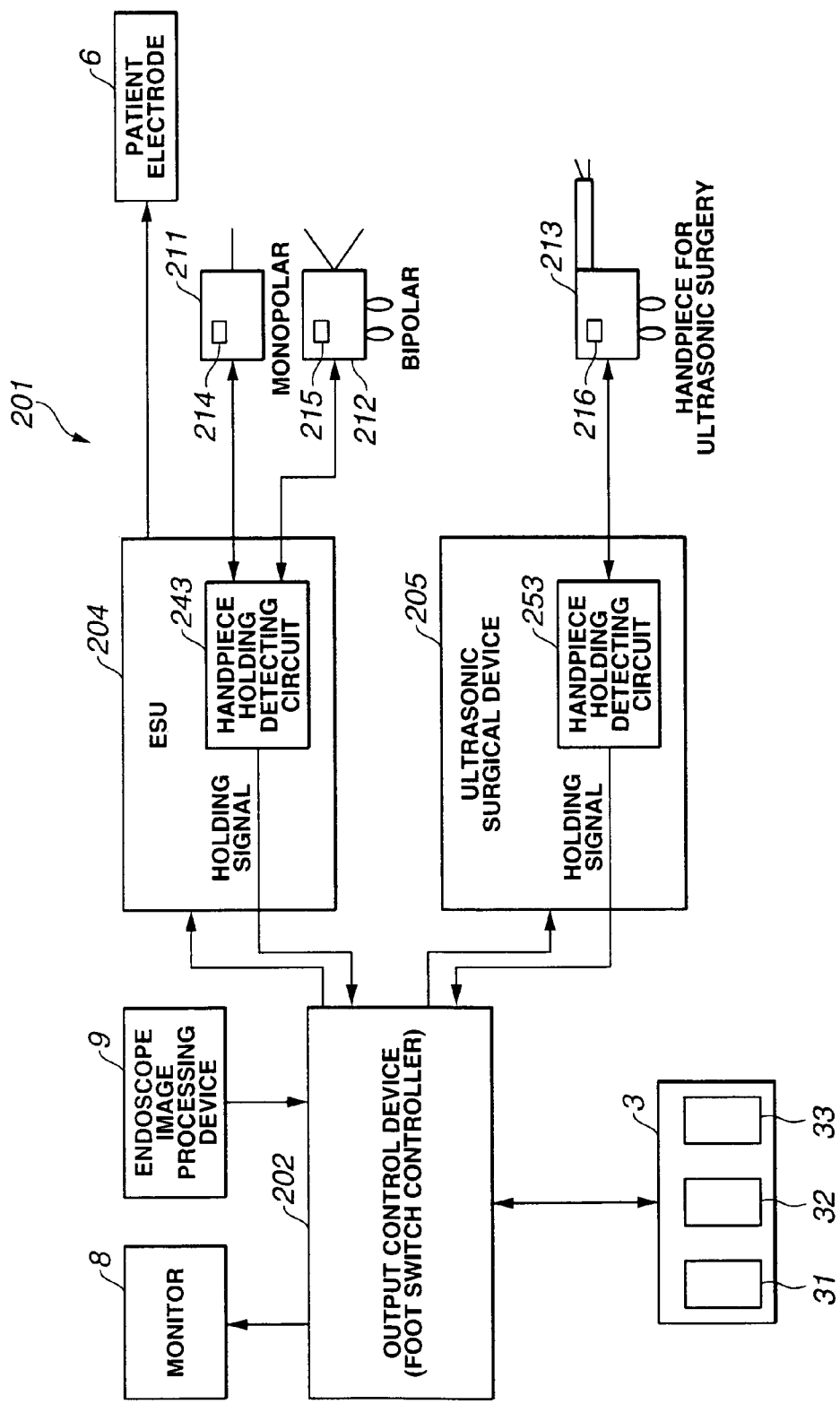

As shown in FIG. 19, a medical system 201 according to the third embodiment detects which handpiece of the handpieces 211 and 212 of an ESU 204 and handpiece 213 of an ultrasonic surgical device 205, is held being and used by the operator, notifies the operator of the detected result, and then automatically maps the setting of the switch pedals of the foot switch 3, i.e., performs switch assignment in accordance with the detected result.

The medical system 201 according to the third embodiment, unlike that in the first embodiment, controls the ESU 204 and the ultrasonic surgical device 205 to perform output respectively using three handpieces of a handpiece 211 for monopolar, a handpiece 212 for bipolar, and a handpiece 213 for ultrasonic surgery.

The handpieces 211 through 213 each include corresponding sensors 214 through 216 for detecting whether or not the handpiece thereof is being held. In contrast, the ESU 204 and the ultrasonic surgical device 205 each include corresponding handpiece holding detection circuits 243 and 253. The handpiece holding detection circuits 243 and 253 detect which handpiece is being held based on detecting signals from the sensors 214 through 216. The detected results of the handpiece holding detection circuits 243 and 253 are transmitted to an output control device 202.

The output control device 202 identifies the handpiece held by the operator based on the detected results received from the handpiece holding detection circuits 243 and 253. Subsequently, as shown in FIGS. 20 and 21, the output control device 202 sets the switch pedals of the foot switch 3, and also displays on the monitor 8 which handpiece is being held by the operator, and how the switch pedals of the foot switch 3 are set.

Description will now be made regarding the setting of the switch pedals of the foot switch 3 using the output control device 202 with reference to FIGS. 20 and 21.

Figure 20:
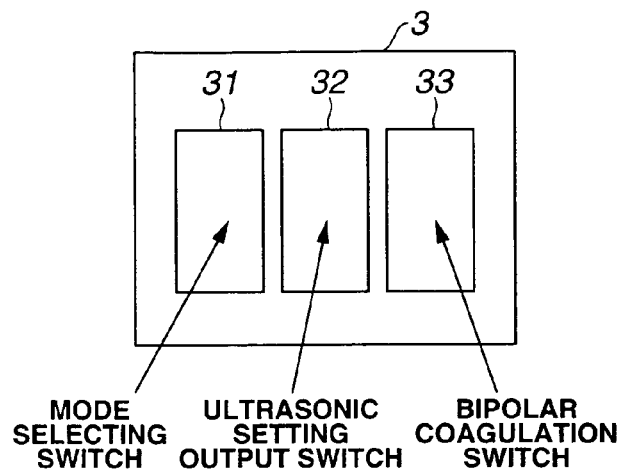
Figure 21:
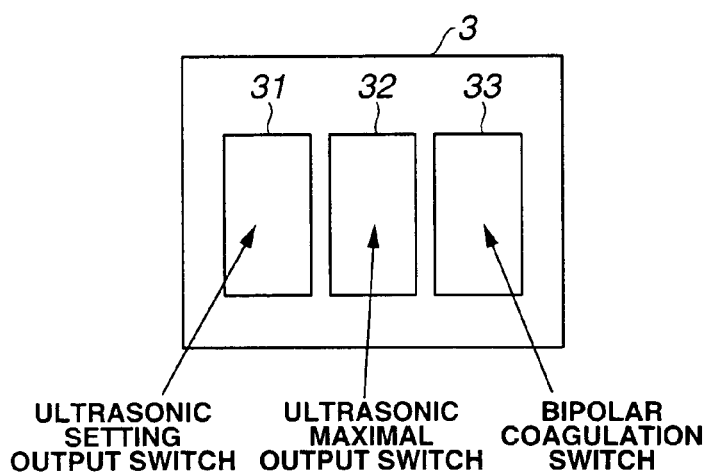

As shown in FIG. 20, with the two-handpiece selection example with mode selection, in the monopolar-and-ultrasonic simultaneous-output mode, the switch pedal 31 of the foot switch 3 has a function for a mode selecting switch.

The switch pedal 32 of the foot switch 3 becomes an ultrasonic setting output switch for controlling the ultrasonic surgical device 205 to perform ultrasonic setting output. The switch pedal 33 of the foot switch 3 becomes a bipolar coagulation switch for controlling the ESU 204 to perform bipolar output for coagulating an affected portion.

On the other hand, as shown in FIG. 21, with the two-handpiece selection example without mode selection, in the monopolar-and-ultrasonic simultaneous-output mode, the switch pedal 31 of the foot switch 3 becomes an ultrasonic setting output switch for controlling the ultrasonic surgical device 205 to perform ultrasonic setting output.

The switch pedal 32 of the foot switch 3 becomes an ultrasonic maximal output switch for controlling the ultrasonic surgical device 205 to perform ultrasonic maximal output, and the switch pedal 33 of the foot switch 3 becomes a bipolar coagulation switch for controlling the ESU 204 to perform bipolar output for coagulating an affected portion.

Figure 8:
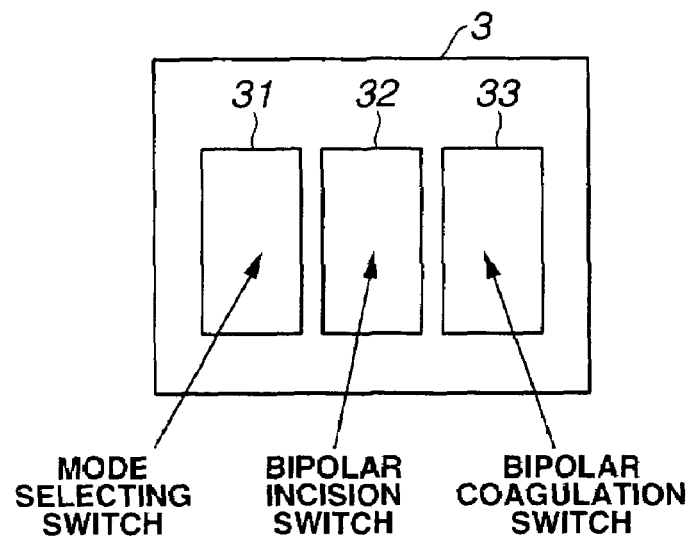
Figure 10:
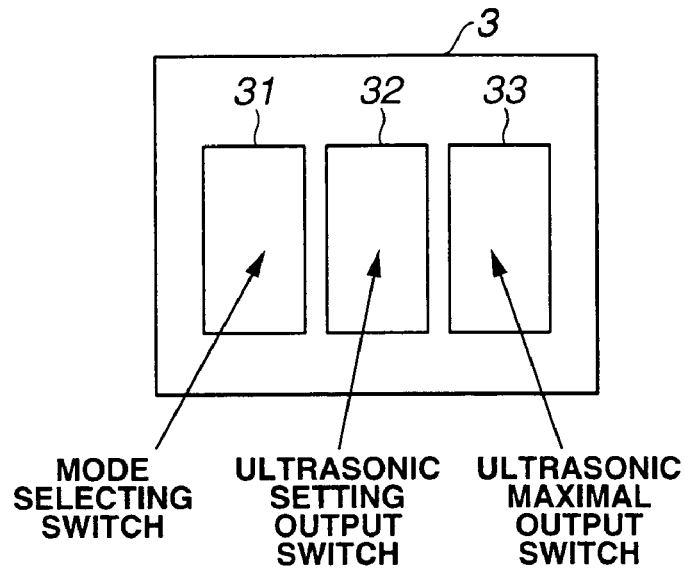

Note that the setting of the foot switch 3 is the same as that in FIGS. 6, 8, and 10 when the selected handpiece is a single. When the operator is not holding any handpiece, the output control device 202 does not perform output regardless which pedal switch provided on the foot switch 3 is operated.

Description will now be made regarding handpiece holding detection means according to the present embodiment with reference to FIG. 22.

The handpiece holding detection means comprises the sensors 214 through 216 provided on the corresponding handpieces 211 through 213, and hand piece holding detection circuits 243 and 253. The holding detection method in this case determines whether or not the operator is holding a handpiece based on variation of capacitance.

The sensors 214 through 216 are preferably installed on a place where the operator touches at the time of treatment, for example, a handle portion for a scissor type handpiece, or a handpiece holding portion for a scalpel type handpiece.

Figure 22:
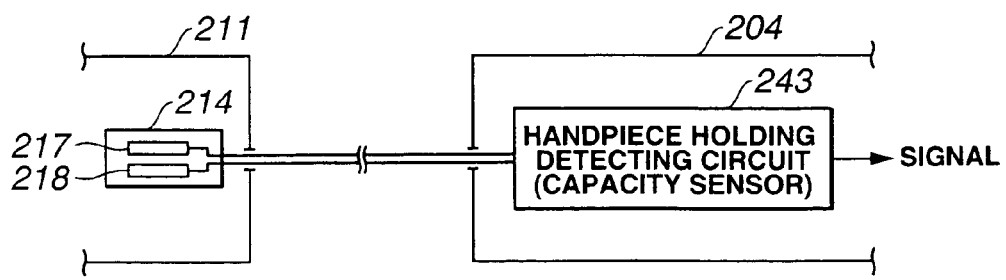

As shown in FIG. 22, two electrodes 217 and 218 are provided within the sensor 214 of the handpiece 211. The capacitance between the two electrodes 217 and 218 varies by the hand of the operator touching near the sensor 214. The handpiece holding detection circuit 243 detects this state, and then generates a holding signal. This holding signal is transmitted from the ESU 204 to the output control device 202.

The output control device 202 detects the handpiece held by the operator based on the input holding signal.

Note that, though not shown in the drawing, the sensor 215 of the handpiece 212 and the sensor 216 of the handpiece 213 include the electrodes 217 and 218 in the same way as those in FIG. 22. The handpiece holding detection circuit 243 within the ESU 204 or the handpiece holding detection circuit 253 within the ultrasonic surgical device 205 detects the capacitance varying by the hand of the operator touching near the sensor 215 or 216, and then generates a holding signal. This holding signal is transmitted from the ESU 204 or the ultrasonic surgical device 205 to the output control device 202.

Description will be made regarding another example of the handpiece holding detection means with reference to FIG. 23.

Figure 23:
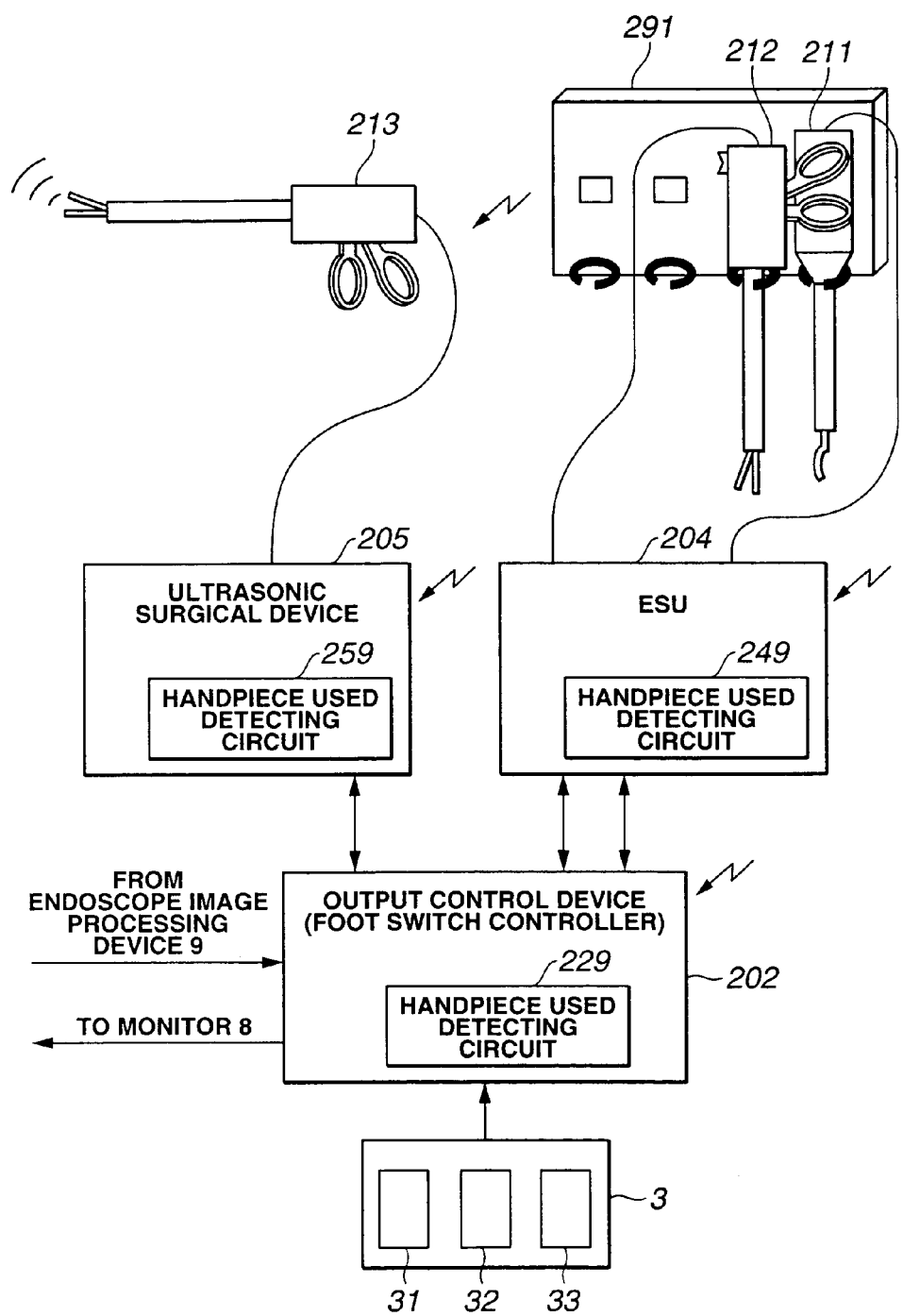

As shown in FIG. 23, in another example of the handpiece holding detection means, a handpiece hanging table 291 is installed in an operating room, for example. The handpieces 211, 212, 213, . . . are disposed at a predetermined position of the handpiece hanging table 291. Thus, when one of the handpieces is detached from the handpiece hanging table 291, the information expressing this state is transmitted to the handpiece used detecting circuits 259, 249, and 229 which are provided in the ultrasonic surgical device 205, the ESU 204, and the output control device 202 respectively.

Note that, in this example shown in FIG. 23, the handpiece hanging table 291 has a configuration wherein an unique installation portion corresponding to each handpiece is provided, and a sensor or the like for detecting whether or not each handpiece is attached is also provided.

The output control device 202 including the handpiece used detecting circuit 229 automatically assigns the switch pedals 31 through 33 of the foot switch 3 to the above-described multiple medical apparatuses in accordance with the detected results in the same way as with the above-described handpiece holding detection means shown in FIGS. 22 and 23.

Operation

Description will be made regarding the processing of the output control device 202 in a case that a first, second, and third handpieces are selected with reference to FIG. 24.

Figure 24:
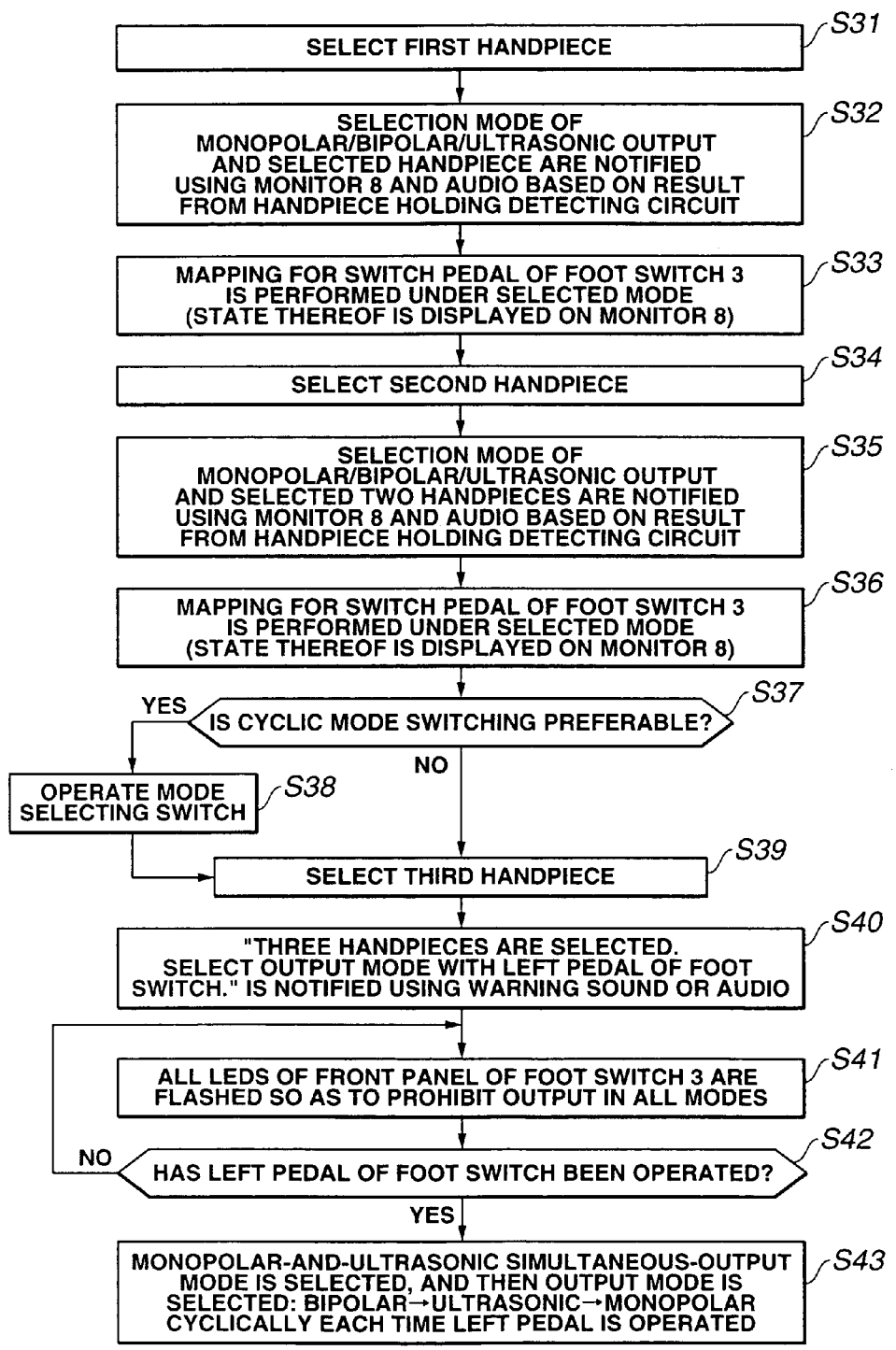

First, as shown in FIG. 24, in Step S31, upon the operator holding a first handpiece, the output control device 202 notifies the operator of the selected mode of monopolar output, bipolar output, or ultrasonic output, and the held and selected handpiece type using the monitor 8 or audio based on the handpiece holding detected results, as shown in Step S32 serving as a holding detection step.

Next, in Step S33, the output control device 202 controls the switch pedals of the foot switch 3 so as to be mapped according to the selected mode. Then, the output control device 202 displays the state on the monitor 8.

Next, as shown in Step S34, upon the operator holding a second handpiece, the output control device 202 notifies the operator of the selected mode of monopolar output, bipolar output, or ultrasonic output, and the held and selected two handpiece types using the monitor 8 or audio based on the handpiece holding detected results in Step S35.

Next, in Step S36 serving as a pedal assigning step, the output control device 202 controls the switch pedals of the foot switch 3 to be mapped according to the selected mode. Subsequently, the output control device 202 assign one of the selected handpieces output to each switch pedal of the foot switch 3. However, in this case, all output settings cannot be assigned to the switch pedals of the foot switch 3. Then, the output control device 202 displays the switch pedal settings of the foot switch 3 on the monitor 8.

Next, in Step S37, the operator determines whether or not the mode is switched cyclically. In a case that the operator does not want to switch the mode cyclically, i.e., in a case that the operator does not operate the mode selecting switch pedal, the flow proceeds to Step S39 without changing the mode switching method.

In Step S37, while the foot switch 3 has been mapped based on the modes of the two selected handpieces, in a case that all output settings are assigned to the foot switch 3 for every mode, i.e., in a case that the operator wants to cyclically select the same pedal setting as that of the time of selecting a single handpiece, the flow proceeds to Step S38. Then, the operator operates the switch pedal 31 set as a mode selecting switch, and performs the mode selection cyclically using the mode selection switch. Subsequently, the flow proceeds to processing in Step S39.

As shown in Step S39, upon the operator holding a third handpiece, the output control device 202 notifies the operator that the third handpiece has been selected using the monitor 8 or audio in Step S40, and further, notifies the operator with a message to the effect of "Three handpieces are selected. Select the output mode with the left pedal (meaning the switch pedal 31) of the foot switch." using a warning sound or audio.

Subsequently, in Step S41, the output control device 202 controls all light emitting diodes (hereafter, referred to as LED) not shown in the drawing, which are provided on the front panel of the foot switch 3, to be a flashing state, prohibits output in all of the modes, and then proceeds to processing in Step S42.

In Step S42, the output control device 202 determines whether or not the switch pedal 31 serving as the left pedal of the foot switch has been operated. Then, the output control device 202 repeats processing in Steps S41 and S42 until the operator operates the switch pedal 31.

In Step S42, upon the operator operating the switch pedal 31, the flow proceeds to processing in Step S43. Then, the output control device 202 cyclically selects the monopolar output mode, the bipolar output mode, and the ultrasonic output mode, which are three output modes, one at a time, and then permits output due to the selected output mode.

That is to say, in the third embodiment, the held handpiece is identified, thereby enabling the setting of the foot switch to be mapped automatically.

Note that in the third embodiment, owing to fixing one of the switch pedals of the foot switch 3 as a mode selection switch, two setting methods can be selected. One is a setting method wherein output mode switching can be performed based on the setting of the switch pedal of the foot switch 3 without performing mode switching cyclically, and the other is a setting method wherein output in all of the modes can be performed by cyclically switching the output mode. However, as shown in FIG. 21, all of the switch pedals 31 through 33 of the foot switch 3 may be assigned as an output switch.

In this case, even if three handpieces are selected, output in all of the modes can be assigned to each switch pedal of the foot switch 3.

In the present embodiment, while the settings of the switch pedals of the foot switch have been automatically mapped in accordance with settings programmed beforehand, mapping is not restricted to this. For example, an arrangement may be made wherein a card slot or the like is provided on the front panel of the output control device 202, mapping data stored in a card beforehand, which is followed by the operator's preference, is read into the output control device 202 by mounting the card on this card slot.

Advantages

According to the third embodiment, the same advantages as of the first embodiment can be obtained, complexity of settings may be reduced by detecting the handpiece held by the operator, and automatically mapping the setting of the switch pedals of the foot switch according to the detected handpiece.

Description will now be made regarding a fourth embodiment of the present invention with reference to FIGS. 25 through 27.

In the first, second, and third embodiments shown in FIGS. 1 through 24, description has been made regarding a case wherein the two devices, i.e., the ESUs 4 and 204, and the ultrasonic surgical devices 5 and 205 are connected to the output control devices 2, 102, and 202. However, in the present embodiment, description will be made assuming that the above-described thermal scalpel 10 and laser surgical device 11 are connected to the output control device as well as the ESU 4 and the ultrasonic surgical device 5.

Figure 25:
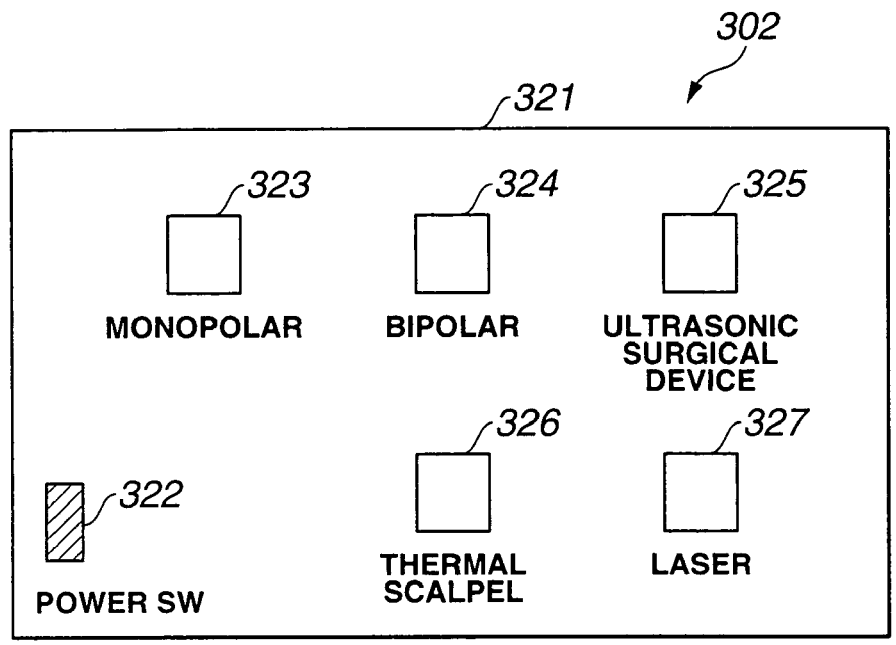

As shown in FIG. 25, a power switch 322, LEDs 323 through 327 are provided on an output control front panel 321 of an output control device 302. The LED 323 indicates whether or not the monopolar output mode is selected. The LED 324 indicates whether or not the bipolar output mode is selected, the LED 325 indicates whether or not the output mode using the ultrasonic surgical device is selected. The LED 326 indicates whether or not the output mode using the thermal scalpel is selected, and the LED 327 indicates whether or not the output mode using the laser surgical device is selected. Note that the above-described LEDs indicate that the corresponding output mode is selected when the LED is in an on state.

Figure 26:
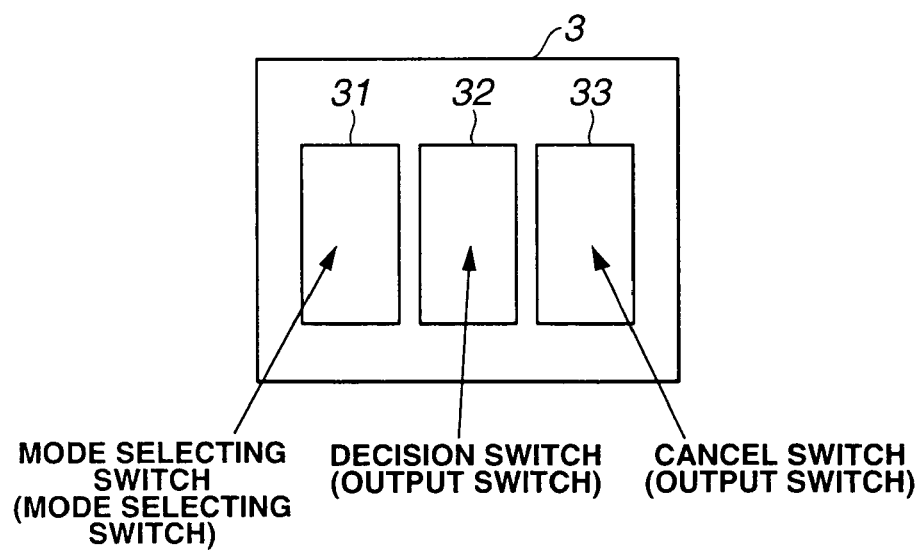
Figure 27:
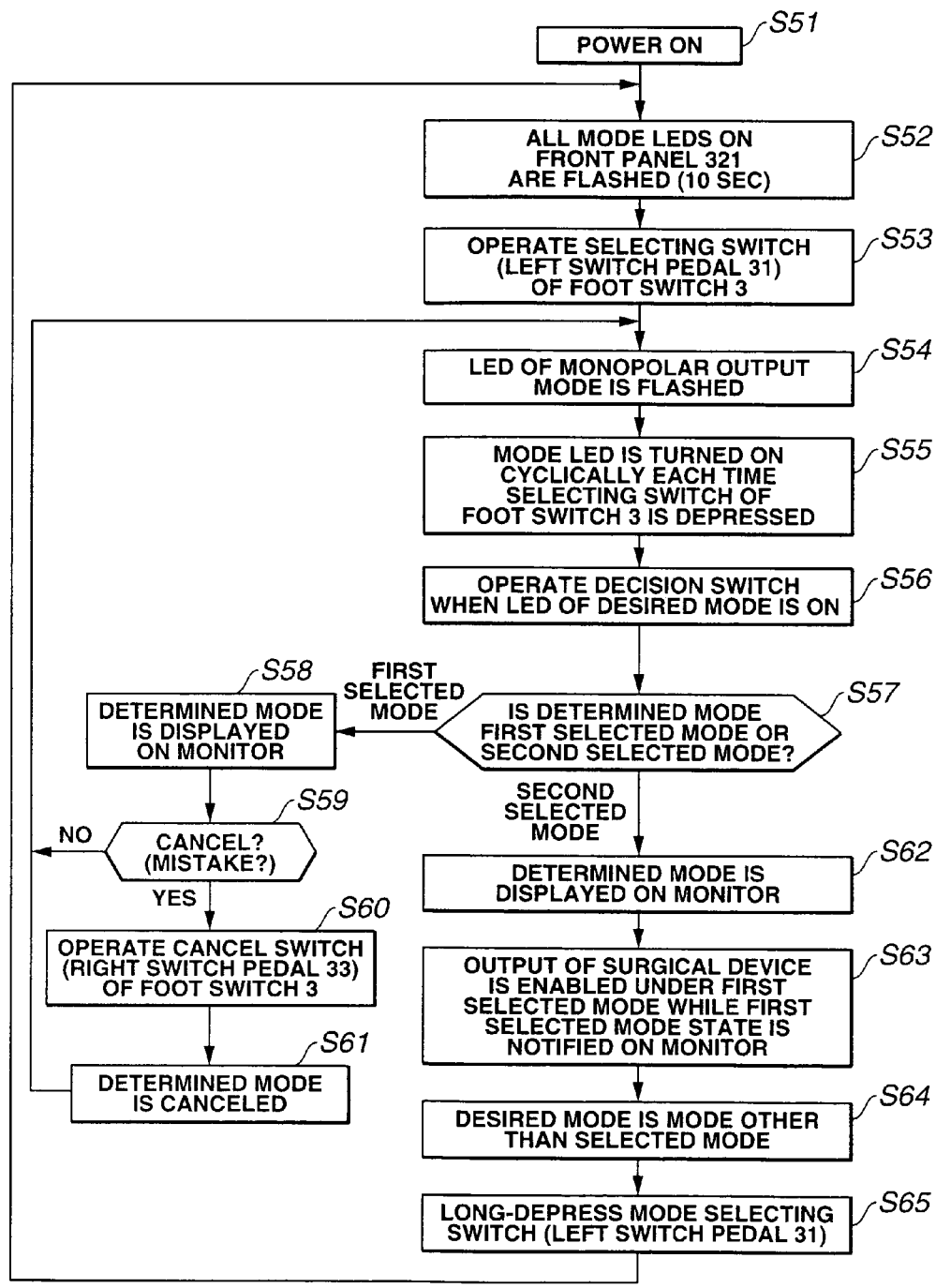

As shown in FIG. 26, the switch pedal 31 of the foot switch 3 has a function as a mode selecting switch when turning power on.

The switch pedal 32 of the foot switch 3 becomes a decision switch for making a decision. The switch pedal 33 of the foot switch 3 becomes a cancel switch for canceling.

The switch pedal 31 of the foot switch 3 has a function as a mode selecting switch even at the time of output as shown in parentheses in the drawing.

On the other hand, the switch pedal 32 of the foot switch 3 becomes an output switch at the time of output as shown in parentheses in the drawing. The switch pedal 33 of the foot switch 3 also becomes an output switch at the time of output as shown in parentheses in the drawing.

According to these settings, up to two desired surgical devices (modes) of the surgical devices connected to the output control device can be selected by the operator operating the foot switch 3 immediately following turning the power of the output control device 302 on.

More specifically, the operator operates the switch pedal 31 which is set as a mode selecting switch of the foot switch 3 so as to select the desired mode. Then, the operator operates the switch pedal 32 which is set as a decision switch of the foot switch 3 so as to decide the selected mode as the desired mode. At this time, in the event that the operator selects the wrong mode, the operator operates the switch pedal 33 which is set as a cancel switch of the foot switch 3 so as to cancel the mode setting.

Operations

Description will now be made regarding processing of the output control device 302 with reference to FIG. 27. First, as shown in FIG. 27, in Step S51, the operator operates the power switch 322 so as to turn power on. In Step S52, the output control device 302 controls all of the LEDs 323 through 327, which indicate the output modes of monopolar, bipolar, the ultrasonic surgical device, the thermal scalpel, and the laser surgical device, which are provided on the front panel 321, to flash. Thus, the operator operates the switch pedal 31 which is set as a mode selecting switch of the foot switch 3 in Step S53. In response to input operation of the switch pedal 31, the output control device 302 proceeds to processing in Step S54.

In Step S54, the output control device 302 controls the LED 323 indicating the monopolar output mode to flash, and controls the LEDs indicating the other output modes to turn off.

In Step S55, the output control device 302 cyclically controls only one of the LEDs 323 through 327 to turn on each time the operator operates the switch pedal 31.

Thus, in Step S56, the operator operates the switch pedal 32, which is set as a decision switch of the foot switch 3, positioned in center when the LED corresponding to the desired mode is turned on. In response to this input operation, the output control device 302 determines the mode for the LED turned on as the desired mode.

Subsequently, in Step S57, the output control device 302 determines whether the mode to be decided is the first selected mode or the second selected mode. When the mode to be decided is the first selected mode, the output control device 302 proceeds to processing in Step S58, and when the mode to be decided is the second selected mode, the output control device 302 proceeds to processing in Step S62.

In Step S58, the output control device 302 displays the first decided mode on the monitor, and then proceeds to Step S59.

In Step S59, the operator determines whether or not to cancel the decided mode. In a case that the operator employs the decided mode, the operator stands by until a predetermined time elapses without any operation. In a case that the operator has not performed any operation for a predetermined time, the output control device 302 determines that the decided mode has been employed, and returns to Step S54 so as to proceed to decision processing of the second selected mode.

In Step S59, in a case that the operator wants to cancel the decided mode, the operator operates the switch pedal 33 which is set as a cancel switch of the foot switch 3, as shown in Step S60. In response to this input operation, the output control device 302 cancels the decided mode as shown in Step S61, and returns to the processing in Step S54.

Next, description will be made regarding processing in a case that the flow proceeds to Step S62 as a result of the determination in Step S57.

Upon proceeding to Step S62, the output control device 302 displays the second decided mode on the monitor, and then proceeds to processing in Step S63. In Step S63, the output control device 302 enables the surgical device to perform output in the first selected mode, and also displays the first decided mode on the monitor.

Subsequently, the flow proceeds to Step S64, in a case that the operator wants to use a mode other than the selected mode, the operator long depresses the switch pedal 31 which is set as a mode selecting switch, as shown in Step S65. In response to this input operation, the output control device 302 returns to the processing in Step S52.

That is to say, in the fourth embodiment, in a case that the operator uses the output mode other than the output mode selected at the time of turning the power of the output control device 302 on, the operator performs a predetermined operation such as long depression of the switch pedal 31 which is set as a mode selecting switch of the foot switch 3, whereby the output control device 302 can return to the initial state when turning power on.

Advantages

According to the fourth embodiment, only a required surgical device can be selected in a state wherein multiple surgical devices are connected to the output control device. Also, a surgical device to be selected is switched to another surgical device as necessary, and moreover, output control can be performed using a single foot switch.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A control device for a medical system comprising:
  an instructing unit, which can be instructed by an operator, for outputting an instructing signal corresponding to the instruction by the operator, the instructing unit includes a mode selection means for selecting one of a singular operation of multiple medical apparatuses and simultaneous operation of multiple medical apparatuses based upon a single depression of a switch, the singular operation of multiple medical apparatuses is selected if the switch is depressed for less than a predetermined period of time, and the simultaneous operation of multiple medical apparatuses is selected if the switch is depressed for greater than the predetermined period of time;

central processing unit for receiving the instructing signal, and generating multiple control signals for controlling multiple medical apparatuses based on the instructing signal; and multiple output units, which can be connected to the medical apparatuses, for outputting the control signals to the medical apparatuses connected thereto.

2. The control device for a medical system according to claim 1, the central processing unit comprising:

simultaneous output control means for controlling the multiple medical apparatuses to perform output simultaneously;

selection output control means for controlling the multiple medical apparatuses to perform output individually; and selection means capable of selecting the simultaneous output control means and the selection output control means based upon a selection signal received from the instruction unit.

3. The control device for a medical system according to claim 2, further comprising a monitor for displaying a set mode, information related to at least one selected medical apparatus, an image of each control switch on the instruction unit and control function associated with each control switch.

4. The control device for a medical system according to claim 1, further comprising a handpiece, which is connected to the multiple medical apparatuses, for receiving output from the multiple medical apparatuses, and subjecting a portion to be treated to medical treatment.

5. The control device for a medical system according to claim 4, further comprising:

a terminal connection detecting circuit, which is provided within the handpiece, for detecting whether or not output from the medical apparatus is connected thereto;

transmission means, provided within the handpiece, for transmitting the detected results output from the detecting circuit to the central processing unit; and warning means, provided in the central processing unit, for performing warning operation in a state wherein the detected results output from the transmission means show that output from the medical apparatus is not connected to the handpiece, and in a case that output control is attempted to the medical apparatus.

6. The control device for a medical system according to claim 4, further comprising:

holding detection means for detecting whether or not the handpiece is held; and switch allocation means for automatically allocating an individual function to switch pedals of a foot switch corresponding to the multiple medical apparatuses in accordance with the detected results from the holding detection means.

7. The control device for a medical system according to claim 4, wherein the handpiece includes at least one of a monopolar terminal or a bipolar terminal.

8. The control device for a medical system according to claim 1, wherein the multiple medical apparatuses include at least one of an electric surgical device, an ultrasonic surgical device, a thermal scalpel, and a laser surgical device.

9. A control method for a medical system for controlling a control device for a medical system to which is connected multiple medical apparatuses, the control method comprising:

a mode selecting step for selecting one of a singular operation of multiple medical apparatuses and simultaneous operation of multiple medical apparatuses with a single depression of a switch, the singular operation of multiple medical apparatuses is selected if the switch is depressed using a single depression for less than a predetermined period of time, and the simultaneous operation of multiple medical apparatuses is selected if the switch is depressed using a single depression for greater than the predetermined period of time;

an instructing signal generating step for generating an instructing signal based upon the depression of the switch;

a simultaneous control signal generating step for generating a simultaneous control signal for controlling multiple medical apparatuses simultaneously in accordance with one instructing signal generated in the instructing signal generating step; and a singular control signal generating step for generating a singular control signal for controlling multiple medical apparatuses individually in accordance with one instructing signal generated in the instructing signal generating step.

10. The control method for a medical system according to claim 9, further comprising:

a detecting step for detecting whether or not output from the medical apparatus is connected to a handpiece, for receiving output from the multiple medical apparatuses which are connected to the control device for a medical system, and subjecting a portion to be treated to medical treatment;

a transmission step for transmitting the detected results in the detecting step to the control device for a medical system; and a warning step to be carried out by the control device for a medical system, for performing warning operation in a state wherein the detected results in the transmission step show that output from the medical apparatus is not connected to the handpiece, and in a case that output control is attempted to the medical apparatus.

* * * * *